US012773123B2

(12) United States Patent
Buckley et al.

(10) Patent No.: US 12,773,123 B2
(45) Date of Patent: Oct. 27, 2026

(54) SURGICAL FLUORESCENCE PROBE FOR TUMOR DETECTION

(71) Applicant: Stryker European Operations Limited, Carrigtwohill (IE)

(72) Inventors: Kevin Buckley, Saint Lukes (IE); Gerard Nunan, Ballincollig (IE); Thomas Stritch, Newmarket (IE)

(73) Assignee: Stryker European Operations Limited, Carrigtwohill (IE)

( * ) Notice: Subject to any disclaimer, the term of this patent is extended or adjusted under 35 U.S.C. 154(b) by 240 days.

(21) Appl. No.: 18/560,872

(22) PCT Filed: May 16, 2022

(86) PCT No.: PCT/IB2022/054542
§ 371 (c)(1),
(2) Date: Nov. 14, 2023

(87) PCT Pub. No.: WO2022/238982
PCT Pub. Date: Nov. 17, 2022

(65) Prior Publication Data

US 2024/0285186 A1 Aug. 29, 2024

Related U.S. Application Data

(60) Provisional application No. 63/188,685, filed on May 14, 2021.

(51) Int. Cl.
*A61B 5/06* (2006.01)
*A61B 5/00* (2006.01)
*A61B 5/1459* (2006.01)

(52) U.S. Cl.
CPC ............ *A61B 5/061* (2013.01); *A61B 5/0071* (2013.01); *A61B 5/1459* (2013.01)

(58) Field of Classification Search
CPC .............................. A61B 5/061; A61B 5/0071
See application file for complete search history.

(56) References Cited

U.S. PATENT DOCUMENTS

| | | | |
|---|---|---|---|
| 5,125,925 | A | 6/1992 | Lundahl |
| 5,200,345 | A | 4/1993 | Young |

(Continued)

FOREIGN PATENT DOCUMENTS

| | | | |
|---|---|---|---|
| JP | 2015505678 | A | 2/2015 |
| KR | 101343868 | B1 | 12/2013 |

(Continued)

OTHER PUBLICATIONS

Bettag, C. et al., "Endoscopic Fluorescence-Guided Resection Increases Radicality in Glioblastoma Surgery", Oper Neurosurg (Hagerstown), vol. 18, No. 1, 2020, pp. 41-46.

(Continued)

*Primary Examiner* — Rochelle D Turchen
(74) *Attorney, Agent, or Firm* — Howard & Howard Attorneys PLLC

(57) ABSTRACT

An optical sensor system for detecting a tissue type in a surgical procedure is described. The optical sensor system includes an excitation source configured to selectively emit excitation light, a probe comprising at least one fiber coupled to the excitation source and configured to illuminate target tissue with excitation light and collect light from target tissue, a compliance member coupled to the at least one fiber, the compliance member being at least partially translucent and configured to deform in response to engagement by a surgical tool, an indicator element configured to emit light in response to receiving an indicator signal, an optical detection module coupled to the at least one fiber and configured to generate a signal based on the collected light, and a controller configured to determine a tissue character- (Continued)

istic based on the signal and generate the indicator signal based on the determined tissue characteristic.

20 Claims, 24 Drawing Sheets

(56) References Cited

U.S. PATENT DOCUMENTS

| | | | | |
|---|---|---|---|---|
| 5,496,997 | A | 3/1996 | Pope | |
| 6,487,428 | B1* | 11/2002 | Culver | A61B 5/0084 600/475 |
| 6,497,715 | B2 | 12/2002 | Satou | |
| 6,955,680 | B2 | 10/2005 | Satou et al. | |
| 6,984,220 | B2 | 1/2006 | Wuchinich | |
| 7,725,162 | B2 | 5/2010 | Malackowski et al. | |
| 8,267,934 | B2 | 9/2012 | Earley et al. | |
| 8,361,070 | B2 | 1/2013 | Hanlon et al. | |
| 8,442,653 | B2 | 5/2013 | Gill | |
| 9,046,448 | B2 | 6/2015 | Takats | |
| 9,216,015 | B2 | 12/2015 | Wilson | |
| 9,763,744 | B2 | 9/2017 | Wilson et al. | |
| 10,918,857 | B2 | 2/2021 | Rapoport et al. | |
| 12,075,980 | B2 | 9/2024 | Amirana et al. | |
| 2007/0078500 | A1* | 4/2007 | Ryan | A61B 5/6853 600/473 |
| 2008/0027346 | A1 | 1/2008 | Litt et al. | |
| 2011/0007312 | A1 | 1/2011 | Bushaw et al. | |
| 2011/0190596 | A1 | 8/2011 | Hacker et al. | |
| 2014/0236024 | A1* | 8/2014 | Bierhoff | A61B 1/00167 600/478 |
| 2014/0276028 | A1* | 9/2014 | Stigall | A61M 25/1006 600/463 |
| 2015/0238085 | A1 | 8/2015 | Inoue et al. | |
| 2016/0206842 | A1* | 7/2016 | Blom | A61B 17/3494 |
| 2018/0057852 | A1 | 3/2018 | Takats et al. | |
| 2019/0192224 | A1* | 6/2019 | Crozier | A61B 18/00 |
| 2019/0267221 | A1 | 8/2019 | Pringle et al. | |
| 2020/0100849 | A1 | 4/2020 | Malackowski et al. | |
| 2020/0261170 | A1 | 8/2020 | Ziso et al. | |

FOREIGN PATENT DOCUMENTS

| | | | |
|---|---|---|---|
| WO | 2020068756 | A1 | 4/2020 |
| WO | 2022190076 | A1 | 9/2022 |

OTHER PUBLICATIONS

Bradley, R.S. et al., "A review of attenuation correction techniques for tissue fluorescence", J R Soc Interface, vol. 3, No. 6, 2006, pp. 1-13.

Brown, T.J. et al., "Association of the Extent of Resection With Survival in Glioblastoma: A Systematic Review and Meta-analysis", JAMA Oncol, vol. 2, No. 11, 2016, pp. 1460-1469.

David, F.G. et al., "Glioblastoma incidence rate trends in Canada and the United States compared with England 1995-2015", Neuro Oncol, vol. 22, No. 2, 2020, pp. 301-302.

English language abstract and machine-assisted English translation for KR 101343868 B1 extracted from espacenet. com database on Jan. 3, 2024, 16 pages.

Ewelt, C. et al., "Finding the anaplastic focus in diffuse gliomas: the value of Gd-DTPA enhanced MRI, FET-PET, and intraoperative, ALA-derived tissue fluorescence", Clin Neurol Neurosurg, vol. 113, No. 7, 2011, pp. 541-547.

Golebiewska, A. et al., "Side population in human glioblastoma is non-tumorigenic and characterizes brain endothelial cells", Brain, vol. 136, Part 5, 2013, pp. 1462-1475.

Henrich, Dominik et al., "Principles of Navigation in Surgical Robotics", Medical Robotics, Navigation and Visualisation, Remagen, Germany, Mar. 11-12, 2004, 10 pages.

Hosmann, A. et al., "5-ALA Fluorescence Is a Powerful Prognostic Marker during Surgery of Low-Grade Gliomas (WHO Grade II)-Experience at Two Specialized Centers", Cancers (Basel), vol. 13, No. 11, 2021, 15 pages.

International Search Report for Application No. PCT/IB2022/054542 dated Aug. 12, 2022, 3 pages.

Jaber, M. et al., "The Value of 5-Aminolevulinic Acid in Low-grade Gliomas and High-grade Gliomas Lacking Glioblastoma Imaging Features: An Analysis Based on Fluorescence, Magnetic Resonance Imaging, 18F-Fluoroethyl Tyrosine Positron Emission Tomography, and Tumor Molecular Factors", Neurosurgery, vol. 78, No. 3, Discussion 411, 2016, pp. 401-411.

Kaneko, S. et al., "Fluorescence real-time kinetics of protoporphyrin IX after 5-ALA administration in low-grade glioma", J Neurosurg,, vol. 136, No. 1, 2022, pp. 9-15.

Louis, D.N. et al., The 2021 WHO Classification of Tumors of the Central Nervous System: a summary:, Neuro Oncol, vol. 23, No. 8, 2021, pp. 1231-1251.

Mcnicholas, K., "In order for the light to shine so brightly, the darkness must be present-why do cancers fluoresce with 5-aminolaevulinic acid?", Br J Cancer, vol. 121, No. 8, 2019, pp. 631-639.

Moradi, Hamid et al., "Toward Robot-Assisted Photoacoustic Imaging: Implementation Using the Da Vinci Research Kit and Virtual Fixtures", IEEE Robotics and Automation Letters, vol. 4, No. 2, Apr. 1, 2019, pp. 1807-1814.

Novotony, A. et al., "Mechanisms of 5-aminolevulinic acid uptake at the choroid plexus", J Neurochem, 2000. vol. 75, No. 1, pp. 321-328.

Reinert, M. et al., "Quantitative Modulation of PpIX Fluorescence and Improved Glioma Visualization", Front Surg, vol. 6, 2019, p. 41.

Richards-Kortum, Rebecca, "Quantitative Optical Spectroscopy For Tissue Diagnosis", Annu. Rec. Phys. Chem. 1996, pp. 555-606.

Roberts, D.W. et al., "Coregistered fluorescence-enhanced tumor resection of malignant glioma: relationships between ?-aminolevulinic acid-induced protoporphyrin IX fluorescence, magnetic resonance imaging enhancement, and neuropathological parameters", Clinical article., J Neurosurg, vol. 114, No. 3, pp. 595-603.

Shah, H.A, et al., "Utility of 5-ALA for fluorescence-guided resection of brain metastases: a systematic review", J Neurooncol, vol. 160, No. 3, pp. 669-675.

Stummer, W. et al., "Technical Principles for Protoporphyrin-IX-Fluorescence Guided Microsurgical Resection of Malignant Glioma Tissue", Acta Neurochir (Wien), vol. 140, 1998, pp. 995-1000.

Stummer, W. et al., "Fluorescence-guided surgery with 5-aminolevulinic acid for resection of malignant glioma: a randomised controlled multicentre phase III trial", Lancet Oncol, vol. 7, No. 5, 2006, pp. 392-401.

Stummer, Walter et al., "Fluouescence-Guided Resection of Glioblastoma Multifome by Using 5-Aminolevulinic Acid-Induced Porphyrins: A Prospectiv Study in 52 Consecutive Patients", J Neurosurg, vol. 93, 2000, pp. 1003-1013.

Stummer, Walter et al., Interoperative Detection of Malignat Gliomas by 5-Aminolevulinic Acid-Induced Porphyrin Fluorescene, Neurosurgery, vol. 42, No. 3, Mar. 1998, pp. 518-526.

Stupp, R et al., "Radiotherapy plus concomitant and adjuvant temozolomide for glioblastoma", N Engl J Med, vol. 325, No. 10, 2005, pp. 987-996.

Traylor, J.I. et al., "Molecular and Metabolic Mechanisms Underlying Selective 5-Aminolevulinic Acid-Induced Fluorescence in Gliomas", Cancers (Basel), vol. 13, No. 3, 2021, 15 pages.

U.S. Appl. No. 18/281,491, filed Sep. 11, 2023.

Utsuki, S. et al., "Histological examination of false positive tissue resection using 5-aminolevulinic acid-induced fluorescence guidance", Neurol Med Chir (Tokyo), vol. 47, No. 5, 2007, Discussion 213-4, pp. 210-213.

Valdes, P.A. et al., "5-Aminolevulinic acid-induced protoporphyrin IX fluorescence in meningioma: qualitative and quantitative measurements in vivo", Neurosurgery, Suppl vol. 1, No. 1, Discussion 82-3, 2014, pp. 74-82.

Valdes, P.A. et al., "Optical technologies for intraoperative neurosurgical guidance", Neurosurg Focus, vol. 40, No. 3, 2016, Page E8.

(56) References Cited

OTHER PUBLICATIONS

Valdes, P.A. et al., “Quantitative fluorescence using 5-aminolevulinic acid-induced protoporphyrin IX biomarker as a surgical adjunct in low-grade glioma surgery”, J Neurosurg, vol. 123, No. 3, 2015, pp. 771-780.
Valdes, P.A. et al., “System and methods for wide-field quantitative fluorescence imaging during neurosurgery”, Opt Lett, vol. 38, No. 15, pp. 2786-278.
Wang, G. et al., “Tumor-associated microglia and macrophages in glioblastoma: From basic insights to therapeutic opportunities”, Front Immunol, vol. 13, 2022, p. 964898.
Widhalm, G. et al., “5-Aminolevulinic acid is a promising marker for detection of anaplastic foci in diffusely infiltrating gliomas with nonsignificant contrast enhancement”, Cancer, vol. 116, No. 6, 2010, pp. 1545-1552.
Zhang, Y. et al., “Single-cell RNA sequencing in cancer research”, J Exp Clin Cancer Res, vol. 40, No. 1, 2021, p. 81.
English language abstract for JP 2015-505678 A extracted from espacenet.com database on Nov. 5, 2025, 2 pages.

* cited by examiner

FIG. 15
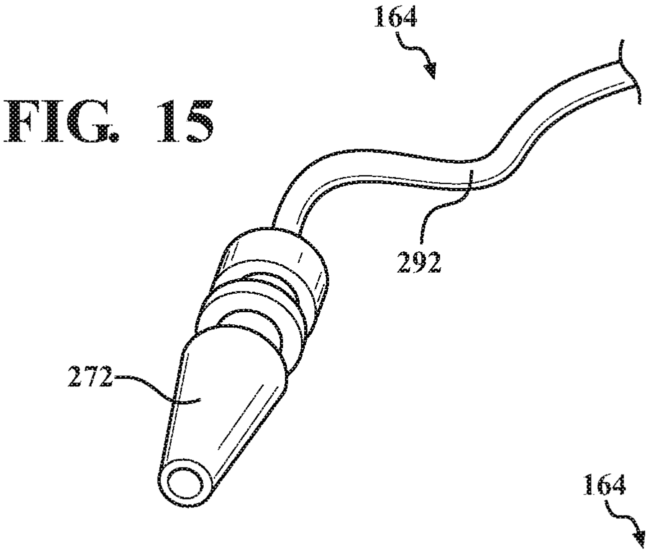
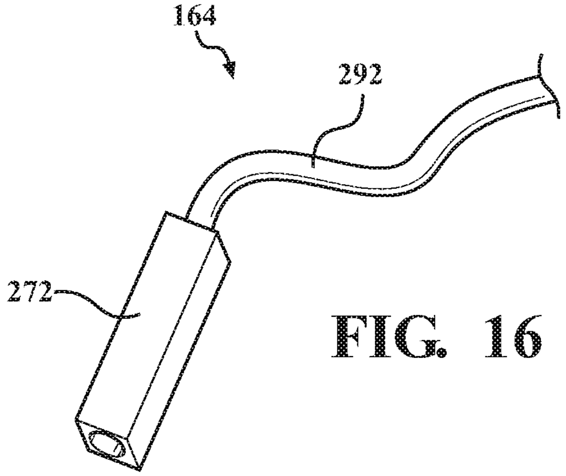
FIG. 16
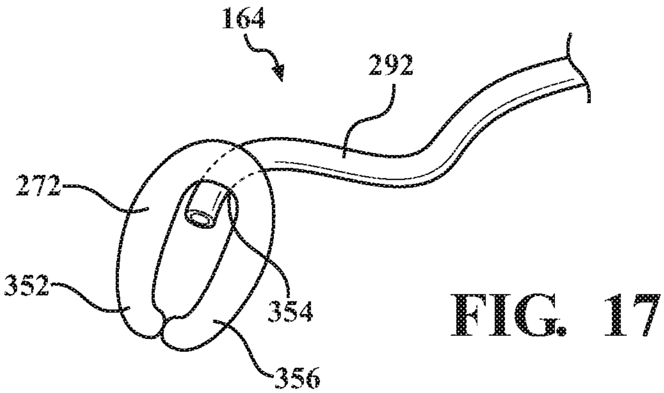
FIG. 17

SURGICAL FLUORESCENCE PROBE FOR TUMOR DETECTION

CROSS REFERENCE TO RELATED APPLICATIONS

This application is the National Stage of International Application No. PCT/IB2022/054542, filed May 16, 2022, which claims priority to and all the benefits of U.S. Provisional Patent Application No. 63/188,685, filed May 14, 2021, the contents of which are hereby incorporated by reference in their entirety.

BACKGROUND

Glioma tumors may start in the glial cells of the brain or the spine. A surgical procedure, more specifically tumor resection, is often performed to resect the tumor. The goal of a surgical procedure for tumor resection is to achieve gross total resection (GTR). A very aggressive form of glioma is glioblastoma. In patients with glioblastoma, GTR has been shown to prolong the life of a patient by about 40% (e.g., from 10 months to 14 months). In patients with lower-grade gliomas, GTR increases the overall chances of survival.

5-Aminolevulinic Acid (5-ALA) is often given to patients a couple hours before surgery. 5-ALA is a compound that occurs naturally in the hemoglobin synthesis pathway. In cancer cells, the hemoglobin synthesis is disrupted and the pathway stalls at an intermediate compound called Protoporphyrin IX (PPIX). During surgery, the healthcare professional may illuminate an area of brain tissue with excitation light (i.e., blue light) from a surgical microscope. The surgery may be carried out in a darkened or dimmed operating room environment. High-grade tumor cells containing PPIX absorb the excitation light and emit red fluorescent light having specific optical characteristics. The fluorescent light may be observed by the healthcare professional from the surgical microscope.

Once the target tissue has been identified, the healthcare professional switches the surgical microscope back to standard white light illumination and continues to resect the target tissue. The healthcare professional switches back and forth between illuminating the tissue with white light and the excitation light throughout the surgical procedure to ensure the appropriate target tissue is being resected until the tumor resection is complete. Each time the target area is illuminated with the excitation light from the surgical microscope, the PPIX present at the tumor site may degrade due to photo-bleaching from being illuminated by the strong excitation light.

Fluorescence guided surgery increases the chances of GTR in high-grade tumors such as with glioblastoma tumors. At present, GTR of lower grade tumors is comparatively low because 5-ALA cannot be used to improve the outcome of lower-grade tumor resection as the tumor cells only emit a low level of fluorescence and the human eye is not sensitive enough to detect such low levels of fluorescence even with the use of the surgical microscope. A need exists for an improved system for fluorescence guided surgery that improves the chances of achieving GTR.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, an optical sensor system for detecting a tissue type in a surgical procedure is described. The optical sensor system includes an excitation source, a probe, an optical detection module, and a controller. The excitation source is configured to selectively emit excitation light. The probe includes at least one fiber that is coupled to the excitation source and that is configured to illuminate target tissue with excitation light and collect light from target tissue. The probe also includes a compliance member that is coupled to the at least one fiber, the compliance member being at least partially translucent and configured to deform in response to engagement by a surgical tool. A portion of the at least one fiber is disposed inside of the compliance member. The probe also includes an indicator element that is disposed at least partially within the compliance member and configured to emit light in response to receiving an indicator signal. The optical detection module is coupled to the at least one fiber and configured to generate a signal based on the collected light. The controller is operatively connected to the optical detection module and configured to determine a tissue characteristic based on the signal and generate the indicator signal based on the determined tissue characteristic.

In a feature, an optical sensor system for detecting a tissue type in a surgical procedure is described. The optical sensor system includes an excitation source, a probe, an optical detection module, and a controller. The excitation source is configured to selectively emit excitation light. The probe includes at least one fiber coupled to the excitation source and configured to illuminate target tissue with excitation light and collect light from target tissue. The probe also includes a sensor body that is coupled to a distal end of the at least one fiber. The probe also includes a tab that is configured to be maneuvered by a surgical tool. The tab being coupled to the at least one fiber proximal to the sensor body. The probe also includes an indicator configured to provide an indication in response to receiving an indicator signal. The optical detection module is coupled to the at least one fiber and configured to generate a signal based on the collected light. The controller is operatively connected to the optical detection module and configured to determine a tissue characteristic based on the signal and generate the indicator signal based on the determined tissue characteristic.

In a feature, an attachment for an optical probe is described. The optical probe includes at least one fiber, an indicator element, and a sensor. The at least one fiber is configured to illuminate target tissue with excitation light and collect fluorescent light from the target tissue. The indicator element is configured to emit an indication light. The sensor body comprising a compliant material that is at least partially translucent in order to allow for at least one of the excitation light, the fluorescent light, and the indication light to pass through. The compliant material being formed of material that is electrically and thermally insulating and configured to deform in response to engagement by a surgical tool.

In a feature, a method for detecting light emitted from brain tissue using an optical sensor system is described. The optical sensor system includes an excitation source, a probe, and an optical detection module. The probe includes at least one fiber that is coupled to the excitation source. The probe further also includes a compliance member that is coupled to the at least one fiber and is deformable. The compliance member is at least partially translucent. The probe further includes an indicator element that is disposed at least partially within the compliance member. The optical detection module is coupled to the at least one fiber and a controller that is operatively connected to the optical detection module. The method includes positioning a suction tool such that the projection is near a lumen of the suction tool. The method further includes applying suction with the suction tool so that the projection becomes disposed within the lumen of the suction tool. The method further includes moving the compliance member with the suction tool to a desired position. The method further includes altering suction of the suction tool such that the suction releases the compliance member. The method further includes emitting, with the excitation source, excitation light. The method further includes illuminating, with the at least one fiber, the brain tissue with the excitation light. The method further includes collecting, with the at least one fiber, fluorescent light from the brain tissue. The method further includes generating, with the optical detection module, a signal based on the collected fluorescent light. The method further includes determining, with the controller, a tissue characteristic based on the signal. The method further includes generating, with the controller, an indicator signal based on the determined tissue characteristic. The method further includes emitting light, with the indicator element, in response to receiving the indicator signal.

In a feature, a method for detecting light emitted from brain tissue using an optical sensor system is described. The optical sensor system includes an excitation source, a probe, and an optical detection module. The probe includes at least one fiber that is coupled to the excitation source. The probe further also includes a compliance member that is coupled to the at least one fiber and is deformable. The compliance member is at least partially translucent. The probe further includes an indicator element that is disposed at least partially within the compliance member. The optical detection module is coupled to the at least one fiber and a controller that is operatively connected to the optical detection module. The method includes engaging the compliance member with a surgical tool such that at least a portion of the compliance member is deformed. The method also includes moving the compliance member with the surgical tool to a desired position. The method also includes emitting, with the excitation source, excitation light. The method also includes illuminating, with the at least one fiber, the brain tissue with the excitation light. The method also includes collecting, with the at least one fiber, fluorescent light from the brain tissue. The method also includes generating, with the optical detection module, a signal based on the collected fluorescent light. The method also includes determining, with the controller, a tissue characteristic based on the signal. The method also includes generating, with the controller, an indicator signal based on the determined tissue characteristic. The method also includes emitting light, with the indicator element, in response to receiving the indicator signal.

In a feature, an optical sensor system for detecting a tissue type in a surgical procedure is described. The optical sensor system includes an excitation source, a probe, an optical detection module, and a controller. The excitation source is configured to selectively emit excitation light. The probe includes at least one fiber that is coupled to the excitation source and that is configured to illuminate target tissue with excitation light and collect light from target tissue. The probe also includes a compliance member that is coupled to the at least one fiber and being at least partially translucent. The compliance member is configured to deform in response to engagement by a surgical tool. A portion of the at least one fiber is disposed inside of the compliance member. The probe also includes an indicator that is configured to provide an indication in response to receiving an indicator signal. The optical detection module is coupled to the at least one fiber and is configured to generate a signal based on the collected light. The controller is operatively connected to the optical detection module and is configured to determine a tissue characteristic based on the signal and generate the indicator signal based on the determined tissue characteristic.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 15 depicts a sample probe of a tissue detection system, the sample probe including a compliance member having a cone shape according to the teachings of the present disclosure.

FIG. 16 depicts a sample probe of a tissue detection system, the sample probe including a compliance member having a rectangular shape according to the teachings of the present disclosure.

FIG. 17 depicts a sample probe of a tissue detection system, the sample probe including a compliance member having an invertible C-shape according to the teachings of the present disclosure.

In the drawings, reference numbers may be reused to identify similar and/or identical elements.

DETAILED DESCRIPTION

The present inventors realized that there exists a need for a neurosurgical tumor resection system and/or method that is capable of detecting low levels of fluorescence in white light operating conditions (i.e., not requiring a darkened or dimmed operating room) while in the process of resecting the tumor. There also exists a need for a system that can reduce the amount of time that the target area is illuminated with excitation light to reduce the effects of photo-bleaching. Additionally, there exists a need for a system that can illuminate excitation light in deep cavities as surgical microscope fail to adequately illuminate excitation light in deep cavities. There also exists a need for a system that assists in intraoperative detection of the anaplastic focus of the tumor which is of importance because finding the anaplastic focus is imperative for precise histopathological diagnosis and optimal patient treatment.

While the disclosure specifically discusses a surgical procedure related to resection of target tissue of a brain tumor with the administration of 5-ALA to visualize fluorescence of PPIX, the teachings of the present disclosure may be extended to other types of surgical procedures, to detect other types of tissue, and to detect other types of fluorophores (Hypericin, Hexvix, Idocyanine Green, etc.). For example, ICG may be administered to help a healthcare professional visualize blood vessels during the surgical procedure. ICG may bond to plasma protein found in blood. ICG is excited by near infrared light and emits near infrared light having a slightly longer wavelength than the near infrared light that excited the ICG.

Figure 1:
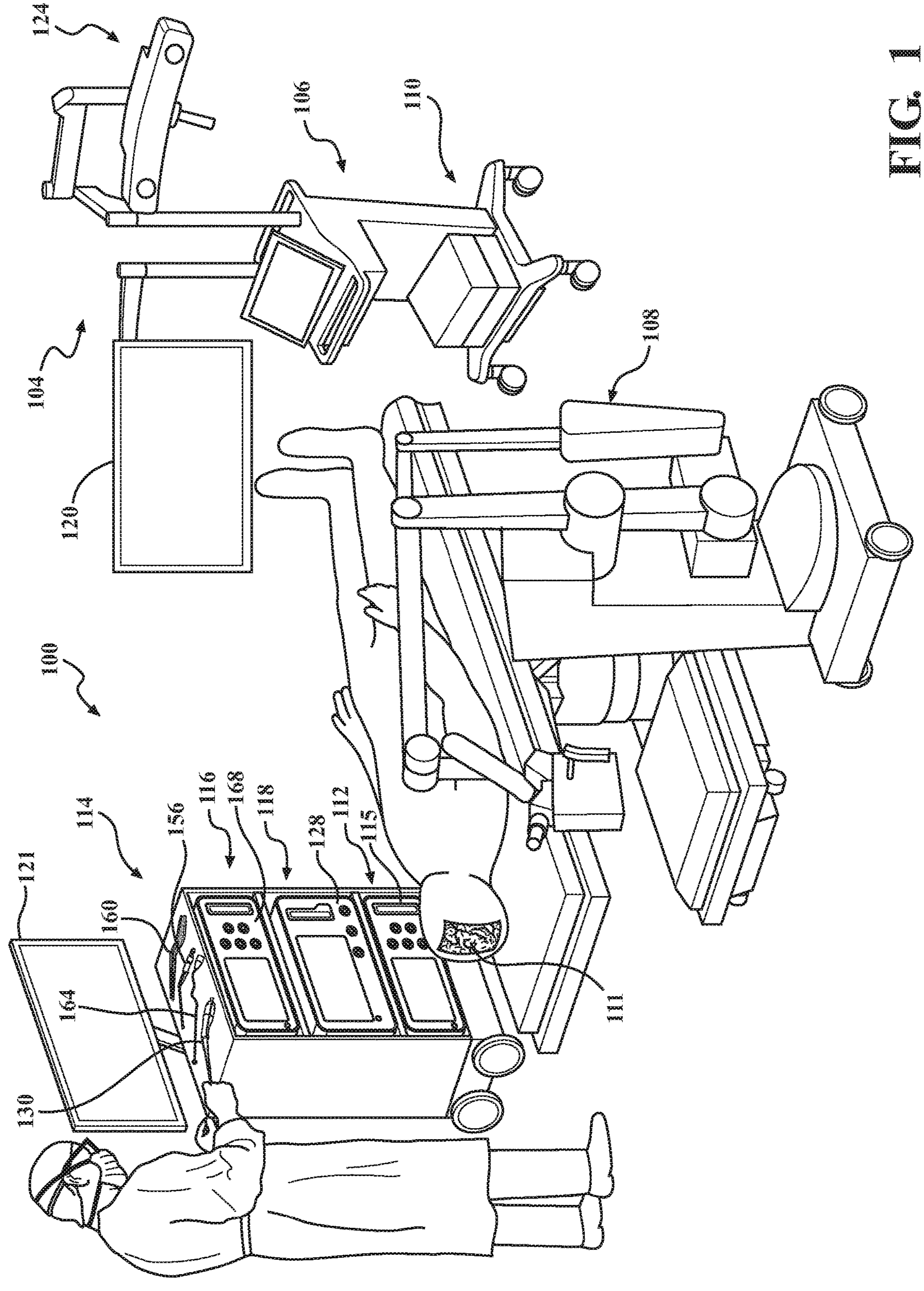
FIG. 1 depicts a neurosurgical system according to the teaching of the present disclosure.

With reference to FIG. 1, the neurosurgical system 100 is provided that solves the shortcomings of the prior art. The neurosurgical system 100 may include a surgical navigation system 104, a surgical microscope 108, and a surgical cart 114. The surgical navigation system 104 includes a cart assembly 106 that houses a navigation computer 110. The navigation computer 110 may also be referred to as the navigation controller. A navigation interface is in operative communication with the navigation computer 110. The navigation interface may include one or more input devices may be used to input information into the navigation computer 110 or otherwise to select/control certain aspects of the navigation computer 110. The navigation interface includes one or more displays 120. Such input devices may include interactive touchscreen displays/menus, a keyboard, a mouse, a microphone (voice-activation), gesture control devices, or the like.

The navigation computer 110 may be configured to store one or more pre-operative or intra-operative images of the brain. Any suitable imaging device may be used to provide the pre-operative or intra-operative images of the brain. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT). The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

The navigation computer 110 may generate the one or more images of the brain on a display 120. The navigation computer 110 may also be connected with the surgical microscope 108. For example, the display 120 may show an image corresponding to the field of view of the surgical microscope 108. When the navigation computer 110 may include more than one display, with one such display showing the field of view of the surgical microscope 108 while the other such display may show a pre-operative or intra-operative image of the brain.

The tracking system 124 is coupled to the navigation computer 110 and is configured to sense the position of one or more tracking elements attached to a surgical tool or the patient. The tracking system 124 may be configured to track active or passive infrared tracking elements attached to the surgical tool or the patient. An example of a surgical navigation system 104 that may be used is Nav3i™ that is commercially available from Stryker. A surgical navigation system 104 may have various functions and features as described in U.S. Pat. No. 7,725,162 B2 and U.S. Pat. Pub. No. 2020/0100849 A1 which are hereby incorporated by reference in their entireties.

The surgical microscope 108 includes one or more objectives configured to provide magnification in a range (e.g., from about 2 times to about 50 times). The surgical microscope 108 can have a field of view having an area of a predetermined range. The surgical microscope 108 is configured for fluorescence microscopy, for example, to detect PPIX. The surgical microscope 108 may include one or more excitation sources (e.g., an excitation source configured to emit light in the visible light spectrum or an excitation source configured to emit light in the infrared spectrum) for illuminating the brain tissue 111 with excitation light to cause the PPIX to fluorescence. The surgical microscope 108 may also include a camera capable of detecting radiation at the fluorescent wavelengths of PPIX or ICG.

The surgical cart 114 may include a surgical system 112, a tissue detection system 116, and an ultrasonic surgical system 118. A display 121 may be coupled to the surgical cart and operatively connected to the surgical system 112, the tissue detection system 116, and the ultrasonic surgical system 118 to display information related with each respective system 112, 116, and 118. A healthcare professional may use the ultrasonic surgical system 118 and/or the surgical system 112 to ablate target tissue of the brain of the patient. The ultrasonic surgical system 118 may include an ultrasonic control console 128 and an ultrasonic handpiece assembly 130.

The surgical system 112 may include a surgical tool and a surgical control console 115 to control various aspects of the surgical tool. The healthcare professional may also use the surgical tool to perform any surgical operation on the tissue. For example, to ablate the tissue, to suction fluid or debris from the tissue, to cauterize the tissue, or combinations thereof. In an example, the surgical system 112 may correspond to a suction system in which the surgical tool corresponds to a suction tool 156 for removing fluid and/or debris from the surgical site. The suction system may have various features, as described in U.S. Pat. No. 8,267,934 B2 which is hereby incorporated herein by reference in its entirety.

In another example, the surgical system 112 may include bipolar forceps 160 as the surgical tool. The bipolar forceps 160 may have features, as described in U.S. Pat. No. 8,361,070 B2 which is hereby incorporated by reference in its entirety. While the disclosure discusses and illustrates that the surgical tool may include a suction tool 156 and bipolar forceps 160, the surgical system 112 and surgical tool may include other tools. In another example, the surgical tool may include a neuro stimulator, a dissector, or an ablation device (e.g., an RF ablation device and/or a laser ablation device). Any number of surgical systems and any number of surgical tools may be employed by the healthcare professional in performing the surgical procedure.

The tissue detection system 116 may include a control console 168 and a sample probe 164. The control console 168 may provide the healthcare professional with a real-time indication when brain tissue 111 corresponds to the target tissue. The tissue detection system 116 determines when the brain tissue 111 corresponds to target tissue based on fluorescent light emitted by the target tissue caused by the fluorophore. In an example, the fluorophore may correspond to PPIX. In another example, the fluorophore may correspond to ICG. Based on the intensity and the wavelengths of the fluorescent light emitted by PPIX, the tissue detection system 116 may determine that the target tissue is present.

Figure 2:
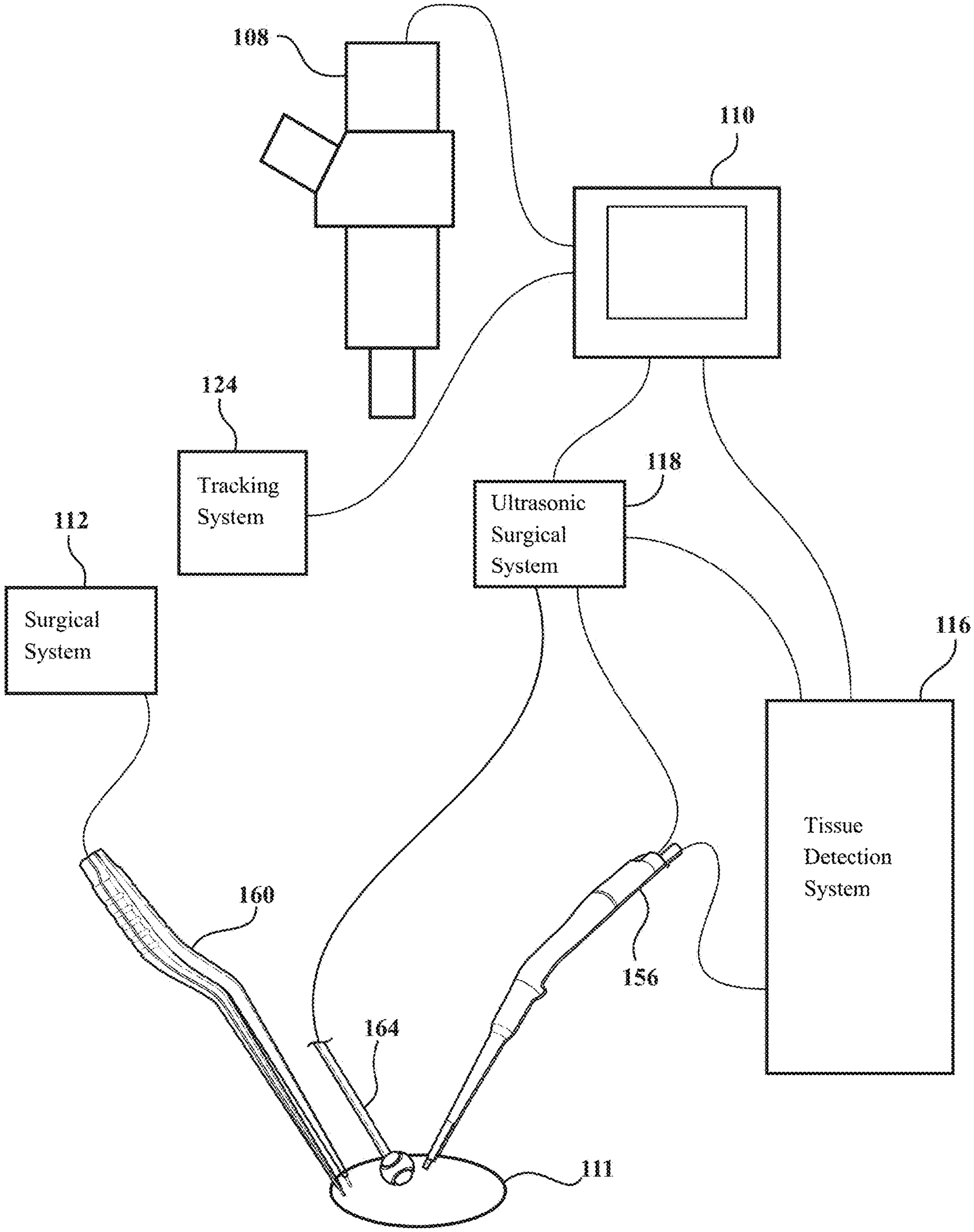
FIG. 2 depicts a functional block diagram of a neurosurgical system according to the teachings of the present disclosure.

With reference to FIG. 2, a schematic of the neurosurgical system 100 is shown. The tissue detection system 116, although capable of performing a similar function (i.e., allowing the healthcare professional to detect the presence of PPIX) to the surgical microscope 108, may be used in conjunction with the surgical microscope 108 to improve the outcome of a tumor resection procedure and the chances of achieving GTR.

During the surgical procedure, the healthcare professional may initially view the brain tissue 111 of the patient with the surgical microscope 108 under excitation light (e.g., the blue light) to identify which portion of the brain tissue 111 corresponds to the target tissue evidenced by the red fluorescent light. The healthcare professional may switch the surgical microscope 108 back to standard white light illumination for better visibility in order to begin resection of the target tissue.

Prior to beginning the resection, the healthcare professional may place the sample probe 164, specifically a compliance member 272 of the sample probe 164, on the target tissue. The healthcare professional may perform the resection of the target tissue with the ultrasonic handpiece assembly 130 in one hand and bipolar forceps 160 in the other hand. During the resection procedure, the healthcare professional may move the compliance member 272 as he/she with either the bipolar forceps 160 or the ultrasonic handpiece assembly 130. The sample probe 164 is designed to be easily engaged by a number of different surgical tools, including but not limited to bipolar forceps, 160, the ultrasonic handpiece assembly 130, and the suction tool 156.

As the healthcare professional is resecting the target tissue, the control console 168 may function to provide the healthcare professional with a real-time indication of the target tissue in the brain tissue 111 via the sample probe 164. The tissue detection system 116 according to the teachings of the present disclosure prevents the healthcare professional from having to switch back and forth between the various illumination settings of the surgical microscope 108 (i.e., illuminating the tissue with excitation light and white light) as the healthcare professional is performing resection of the target tissue. This becomes especially important as the healthcare professional approaches the margin of the target tissue because it is desirable for the healthcare professional to achieve GTR (resect all of the target tissue) but to leave as much healthy tissue intact as possible.

Figure 3:
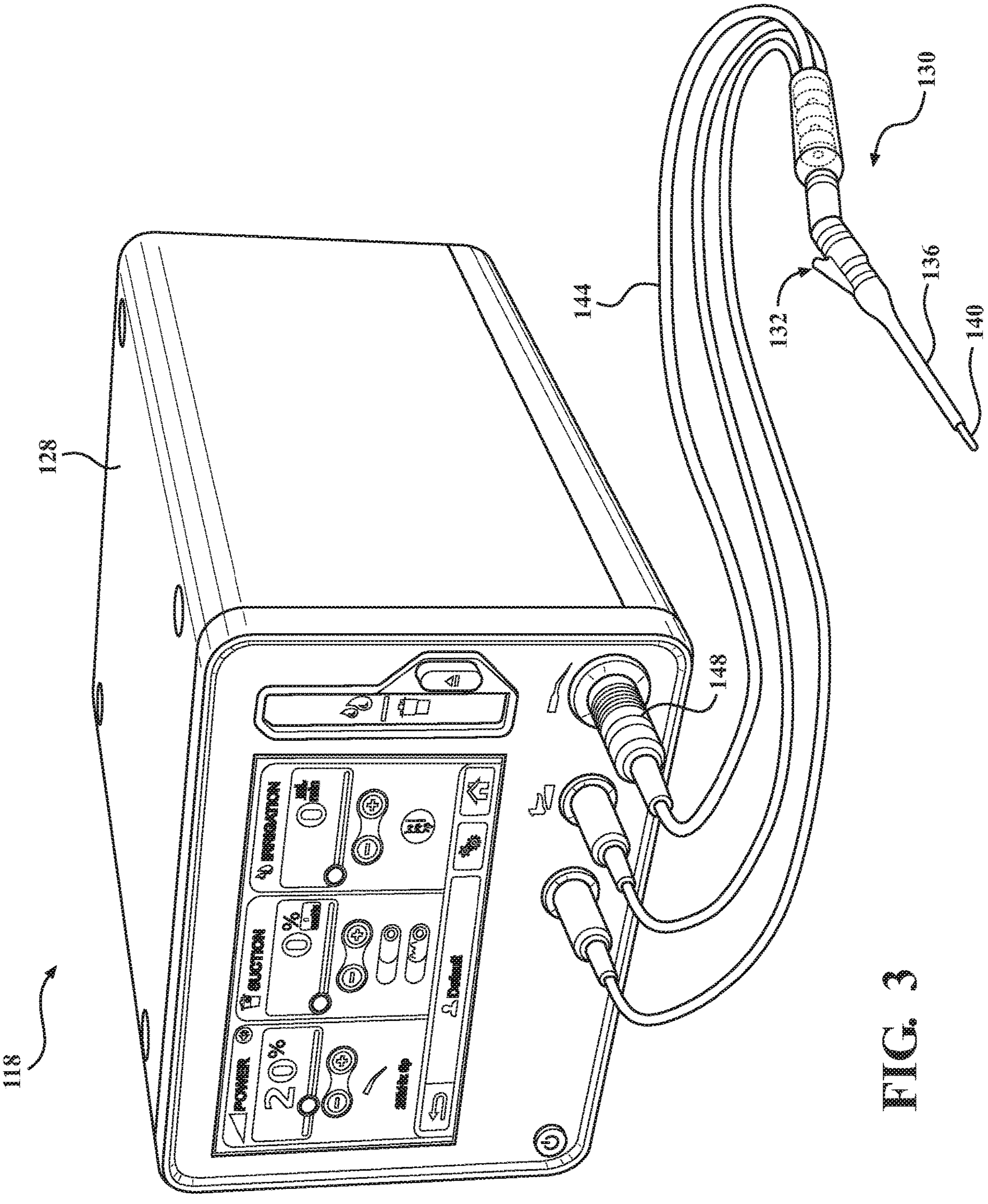
FIG. 3 depicts an ultrasonic surgical system of a neurosurgical system according to the teachings of the present disclosure.

With reference to FIG. 3, the ultrasonic handpiece assembly 130 may comprise an ultrasonic handpiece 132 comprising a proximal end and distal end. The ultrasonic handpiece assembly 130 may further comprise a sleeve 136 and an ultrasonic tip 140 that may be coupled to the distal end of the ultrasonic handpiece 132. The sleeve 136 may be configured to provide irrigation to the ultrasonic tip 140 and/or the surgical site. It is further contemplated that the sleeve 136 may also be configured to provide aspiration to the ultrasonic tip 140. The ultrasonic tip 140 may comprise a cutting feature that is configured to ablate, cut, shape, and/or remove biological tissue. The ultrasonic handpiece assembly 130 may have various features, as described in U.S. Pat. Nos. 6,497,715 B2; 6,955,680 B2; and 6,984,220 B2 and PCT Publication WO 2020/068756 A1; which are hereby incorporated herein by reference in their entirety.

The ultrasonic handpiece assembly 130 may also comprise a cable 144 or other power cord comprising a power connector 148 or adapter configured to couple the ultrasonic handpiece assembly 130 to a power supply, such as the ultrasonic control console 128 configured to regulate the various aspects of the ultrasonic handpiece assembly 130. The ultrasonic control console 128 may also be configured to regulate the irrigation and/or aspiration functions of the ultrasonic handpiece assembly 130 to optimize performance of the ultrasonic handpiece assembly 130. An example of ultrasonic surgical systems that may be used are commercially available from Stryker including Sonopet IQ Ultrasonic Aspirator. The ultrasonic control console 128 may control various operation parameters based on signals received from the tissue detection system 116.

Figure 4:
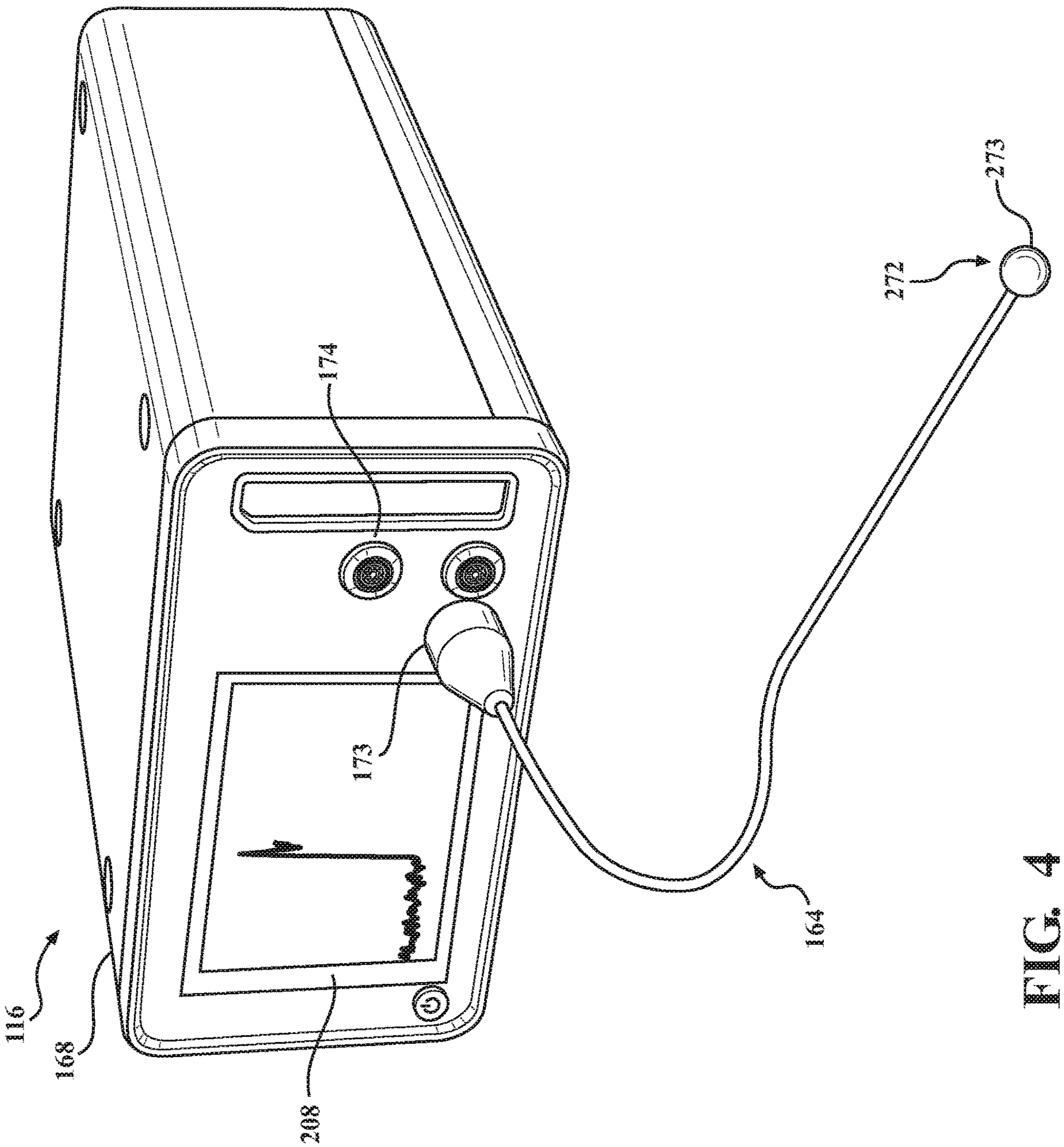
FIG. 4 depicts a tissue detection system of a neurosurgical system according to the teachings of the present disclosure.
Figure 5:
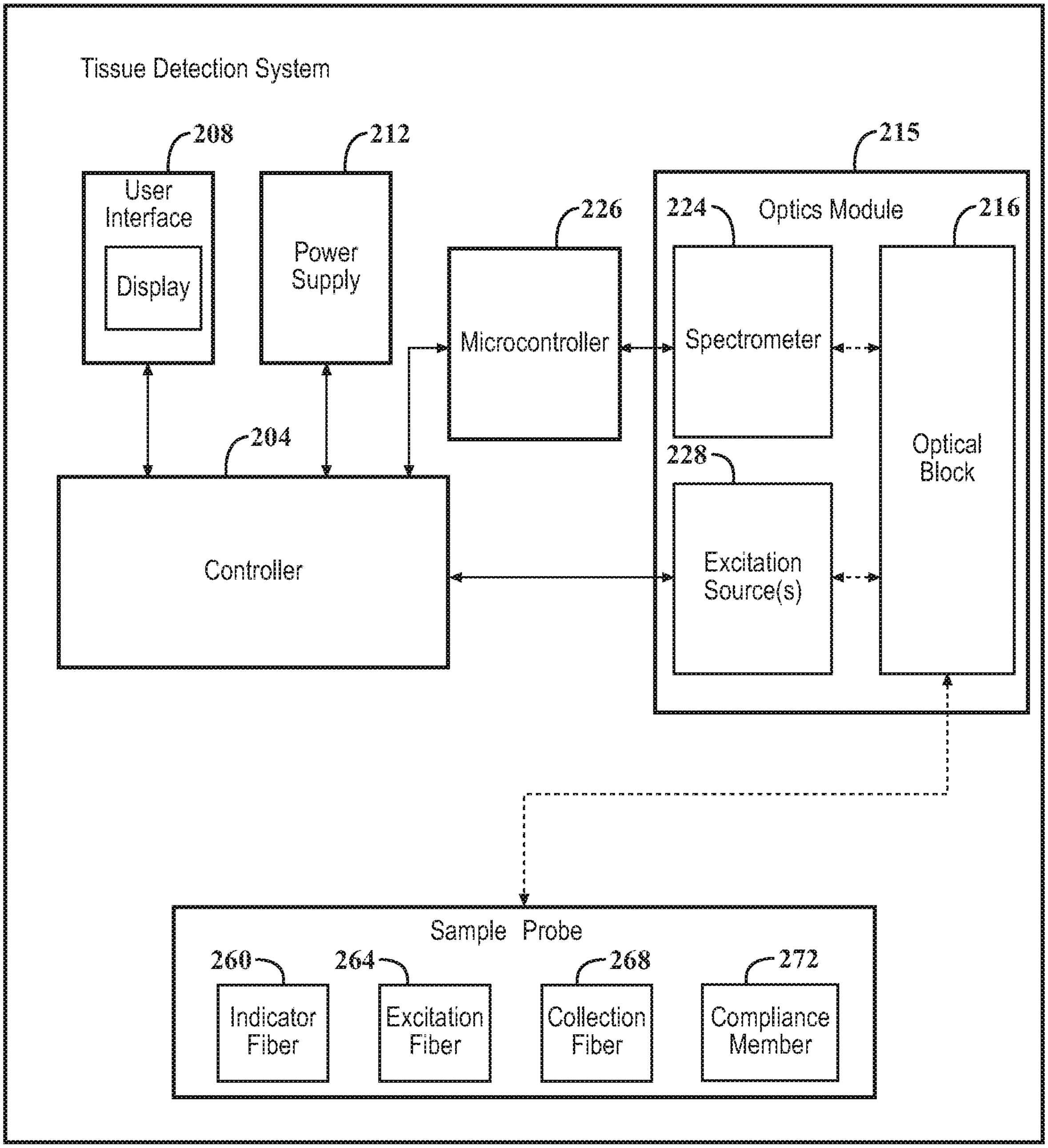
FIG. 5 depicts a functional block diagram of a tissue detection system of a neurosurgical system according to the teachings of the present disclosure.

With reference to FIGS. 4 and 5, the tissue detection system 116 includes a sample probe 164 and a control console 168. The sample probe 164 is connected to the control console 168 via the connector 299. The sample probe 164 includes an indicator fiber 260, an excitation fiber 264, a collection fiber 268, and a compliance member 272. The control console 168 may include a controller 204, a user interface 208, a power supply 212, an optics module 215, and a microcontroller 220. The optics module 215 may include an optics block 216, a spectrometer 224, an excitation source 228, and an optical connector 229. The function of each component will be discussed in greater detail below.

The user interface 208 may include a display for displaying output from the controller 204 or microcontroller 226, which may be integrated into a single device or communicate with one another. The user interface 208 may also include one or more inputs (e.g., a push button, a touch button, a switch, etc.) configured for engagement by the healthcare professional. The power supply 212 may supply power to various components of the control console 168. The control console 168 may include a probe port 173 in which the connector 299 of the sample probe 164 is connected. The fibers 260, 264, 268 may then be connected to the optics block 216 via the optical connector 229. The control console 168 may also include an electrical port 174 for establishing a communication link to the surgical system 112, the ultrasonic surgical system 118, or any other system.

The excitation source 228 may illuminate the target tissue with excitation light via the excitation fiber 264. The excitation source 228 may be configured to emit the excitation light (e.g., blue light at about 405 nm or blue light in the range of 400 nm to 500 nm. The excitation source 228 may also be configured to emit excitation light corresponding to other wavelengths such as wavelengths associated with the rest of the visible light spectrum other than blue light (e.g., greater than 500 nm but less than 700 nm), wavelengths associated with ultraviolet light spectrum (less than 400 nm) and/or infrared light spectrum (greater than 700 nm). The excitation source 228 may include any number of light sources such as a light emitting diode (LED), a pulsed laser, a continuous wave laser, a modulated laser, a filtered white light source, etc.

The excitation source 228 is operable in different states, the different states including at least one of an on state, an off state, a first flashing state in which light is emitted at a first frequency, a second flashing state in which light is emitted at a second frequency different than the flashing state, a first intensity state in which light is emitted at a first intensity, a second intensity state in which light is emitted at a second intensity different than the first intensity, and different color states (i.e., different wavelengths) as described above.

When the excitation source 228 includes a plurality of excitation sources such as a first excitation source, a second excitation source, and a third excitation source, the first excitation source may be configured to emit a first excitation light at the predetermined wavelength of the visible light spectrum, the second excitation source may be configured to emit infrared light at a second wavelength range corresponding to the infrared light spectrum (e.g., 700 nm to 1 mm) and the third excitation source may be configured to emit a third excitation light at a predetermined wavelength of the visible light which is different than the first predetermined wavelength. Stated differently, the first excitation source may be configured to emit light which would excite a first fluorophore such as PPIX, the second excitation source may be configured to emit visible light at a second predetermined wavelength, the second predetermined wavelength representing, for example, green light and the third excitation source may be configured to emit infrared light which would excite a second fluorophore, such as ICG.

The controller 204 may control operation of the excitation source 228 such as to operate the excitation source 228 in one of the previous mentioned states. The controller 204 may control operation of the excitation source 228 by varying operating parameters of the excitation source 228. The operating parameters may correspond to a time setting, a power setting, or another suitable setting. The time setting may include a pulse width. The pulse width may be based on the integration time of the spectrometer 224. The integration time of the spectrometer 224 is discussed in greater detail below.

Figure 6A:
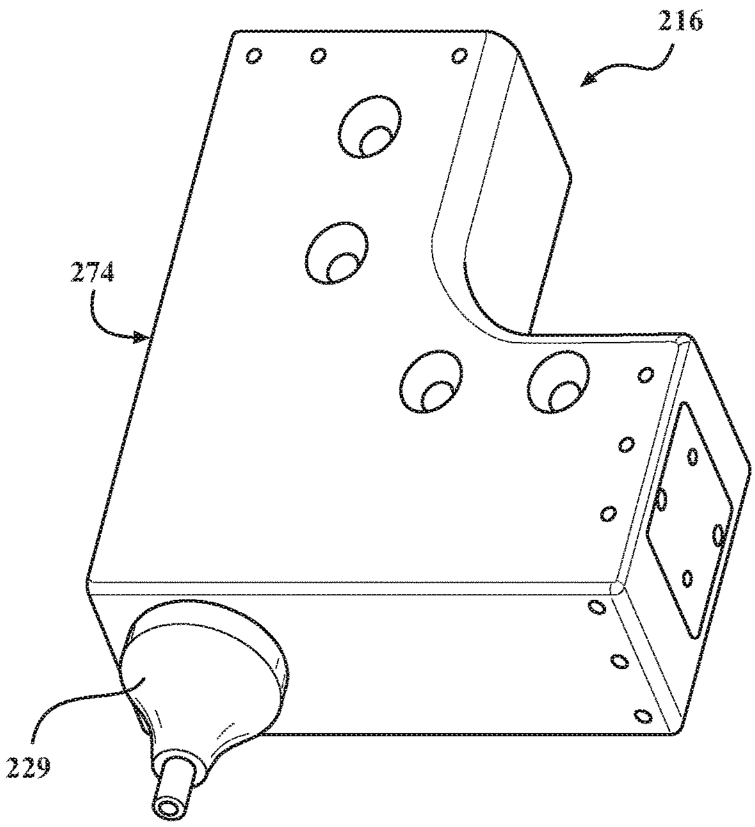
FIGS. 6A and 6B depict an optical module of a tissue detection system according to the teachings of the present disclosure.
Figure 6B:
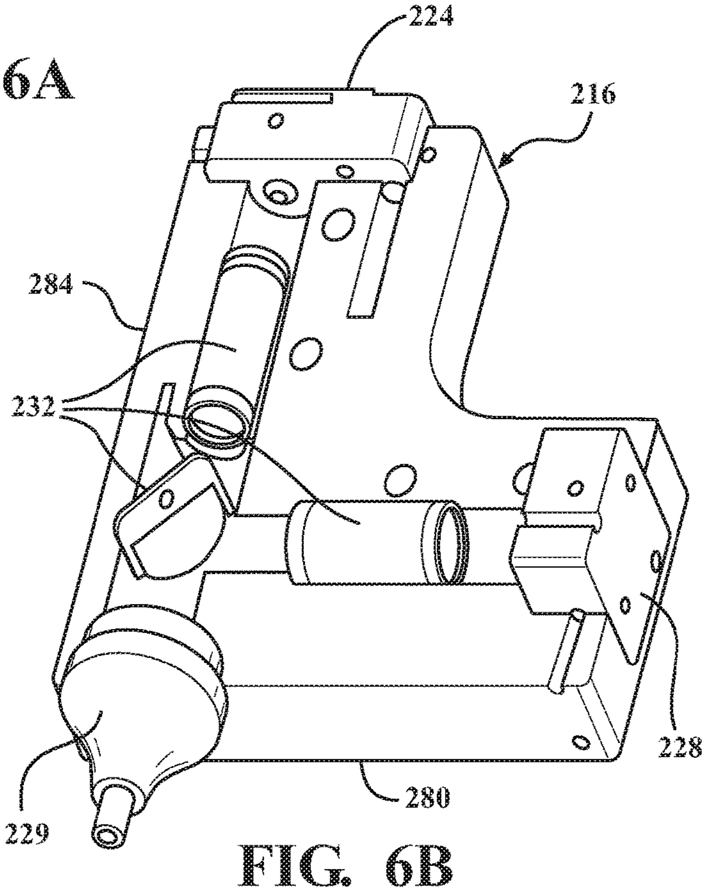

With reference to FIGS. 6A and 6B, the optics block 216 is shown. The optical connector 229 may be coupled to the optics block 216. The optics block 216 may include an outer casing 274 constructed of metal or another suitable material and may fully enclose components 232 of the optics block 216. FIG. 7B shows the optics block 216 with the top of the casing removed such that the components 232 of the optics block 216 are visible. The optics block 216 may be L-shaped and include a first portion 280 and a second portion 284. The excitation source 228 may be coupled to the first portion 280 of the optics block 216. The spectrometer 224 may be coupled to the second portion 284 of the optics block 216.

Figure 7A:
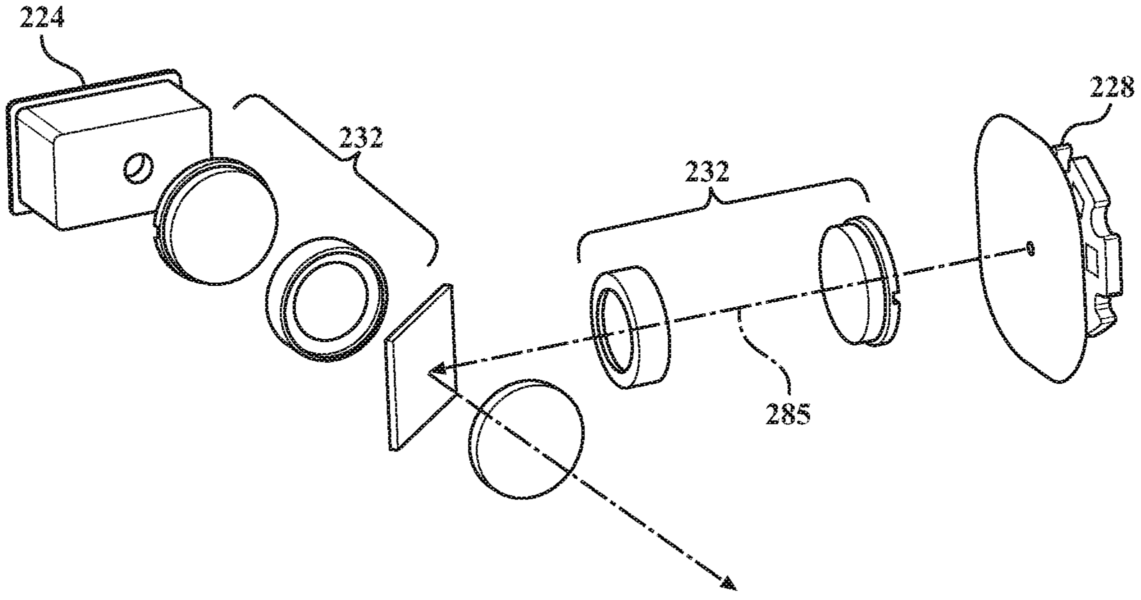
FIGS. 7A and 7B depict an exploded view of some components of the optical module of a tissue detection system according to the teachings of the present disclosure.
Figure 7B:
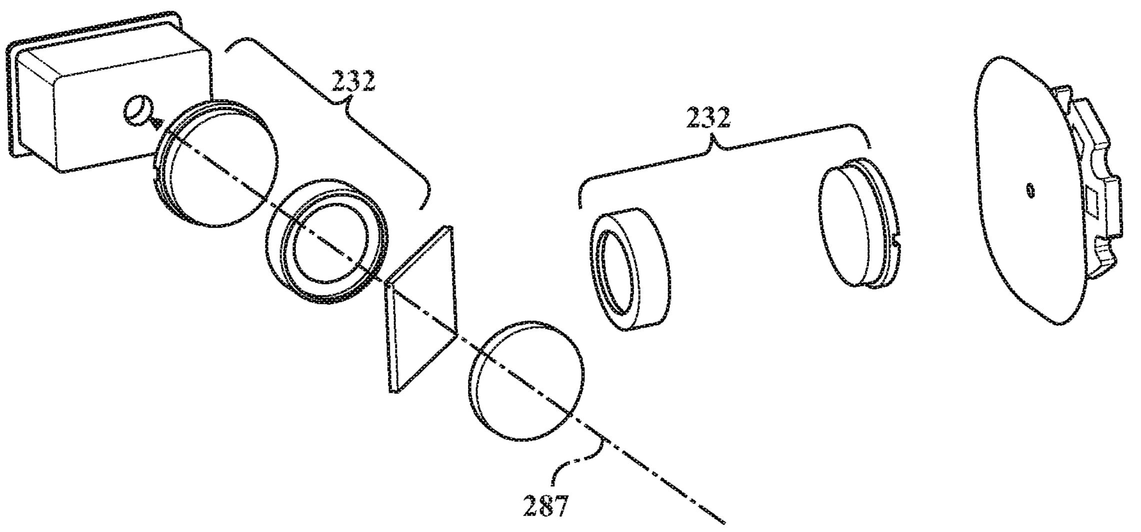

With additional reference to FIGS. 7A and 7B, an exploded view of the components 232 of the optics module 215 is shown illustrating an optical path 285 for the excitation light and the optical path 287 for the collected light from the brain tissue 111. The first portion 280 may include the optical path 285 for the excitation light to travel from the one or more excitation sources 228 to the brain tissue 111 via the excitation fiber(s) 264. The optical path 285 may be defined by the components 232 in the first portion 280 of the optical block. The second portion 284 may include the optical path 287 for the collected light to travel from the brain tissue 111 via the collection fiber 268 to the spectrometer 224. The optical path 287 may be defined by the components 232 in the second portion 284 of the optical block. The components 232 of the optical block may include any optical components such as a laser line filter and one or more long-pass filters. The optics block 216 may include other optical components such as one or more mirrors, lenses, optical connectors, optical fiber, and/or any other suitable optical components.

In FIG. 7A, the excitation source 228 emits the excitation light which travels through one or more components 232, such as a laser line filter and/or long pass filter. The laser line filter or bandpass filter may be configured to reject unwanted noise (e.g., lower level transitions, plasma, and glows) generated by the excitation source 228. Stated differently, the laser line filter may be configured to clean up the excitation light or make the excitation light more monochromatic. The long-pass filter may be configured to reflect the light down the excitation fiber 264 and to the brain tissue 111. The excitation source 228 may be configured to deliver unfiltered excitation light (i.e., the filters may be omitted) via the excitation fiber 264 to the target tissue. The excitation fiber 264 may guide the excitation light to the brain tissue 111 via the sample probe 164.

The collection fiber 268 may be configured to collect light (i.e., fluorescent light and ambient light) from the brain tissue 111 after the tissue has been excited. Due to the presence of ambient light and/or background light caused by various sources in the operating room such as the surgical microscope 108, surgical lamps, or any other devices in the operating room, the light collected from the brain tissue 111 may include the ambient light and/or background light. With reference to FIG. 7B, the light collected by the collection fiber passes through the components 232, such as the long pass filter, of the second portion 284 of the optics block 216. After the light passes through the components 232, the light may enter the spectrometer 224 which is coupled to the optics block 216.

While the example is provided that the excitation fiber 264 and the collection fiber 268 are described as separate fibers, a single fiber may be provided and configured to perform the functions of the excitation fiber 264 and the collection fiber 268. In this configuration one or more other optical components may be necessary. While the excitation fiber 264, the collection fiber 268, and the indicator fiber 260 are discussed as a single fiber for simplicity, it is understood that there may be more than one fiber. For example, the excitation fiber 264 may include a bundle of excitation fibers, the collection fiber 268 may include a bundle of collection fibers, and the indicator fiber 260 may include a bundle of indicator fibers all being connected in similar fashion to the single fiber connections discussed above. In another example, the excitation fiber 264 may include any number of fibers connected in series, the collection fiber 268 may include any number of fibers connected in series and the indicator fiber 260 may include any number of fibers connected in series.

The spectrometer 224 is configured to convert the filtered optical signals (i.e., filtered light) into spectral signals in the form of electrical signals. The microcontroller 220 is configured to control operation of the spectrometer 224. Examples of spectrometer systems that may be used are commercially available from Hamamatsu including Mini-spectrometer micro series C12880MA. The spectrometer 224 may include an entrance slit, a collimating lens/mirror, transmission grating element, a focusing mirror, and an image sensor. The entrance slit may receive the collected light from the optics block 216 which then passes through the collimating lens/mirror. The collimating lens/mirror collimates the collected light passed through the entrance slit and guides it onto the grating element. The grating element separates the incident light from the collimating lens into different wavelengths and lets the light at each wavelength pass through or reflect away at a different diffraction angle. The focusing lens or mirror forms an image of the light dispersed into wavelengths by the grating element onto linearly arranged pixels of the image sensor according to wavelength.

Each wavelength is photoelectrically converted into an electrical signal (i.e., a spectral signal). The image sensor outputs the signal of light incident on each pixel at a certain time interval (i.e., the image sensor converts the optical signals into electrical signals and outputs them). The time interval may be referred to as the integration timing. The microcontroller 220 may be configured to control operation of the spectrometer 224, for example, the integration timing based on instructions from the controller 204. The microcontroller 220 forwards the spectral signals via a communication interface (e.g., serial peripheral interface (SPI)) to the controller 204.

As described previously, since ambient light may be present in the optical signals collected at the target tissue and thus present in the spectral signals provided by spectrometer 224, the controller 204 may be configured to perform one or more functions or methods of control to remove the ambient light or noise from the spectral signals (i.e., the wavelengths associated with the ambient light) to accurately detect when the brain tissue 111 corresponds to the target tissue as evidenced by the PPIX present in the target tissue. The spectral signals after ambient light has been removed may be referred to as modified spectral signals.

The controller 204 may generate an indication signal based on the modified spectral signals. For example, the controller 204 may compare the PPIX intensity to a predetermined intensity threshold and in response to the PPIX intensity exceeding the threshold, the controller 204 may generate an indication signal. The excitation sources 228 may emit light which travels down the indicator fiber 260 and illuminates a portion of the sample probe 164 in response to receiving the indication signal. For example, the controller 204 may control the excitation source 228 to emit green light (e.g., wavelengths of about 520-564 nm) when PPIX above a threshold is detected or yellow light (e.g., wavelengths 565-590 nm) when ICG is detected. Alternatively, as described above, the controller 204 may control an indicator other than one coupled to an indicator fiber, such as controlling a light source, i.e., turning on a light source on the probe in response to receiving the indication signal.

The controller 204 may communicate with the ultrasonic control console 128 via a communication link established through the electrical port 174. For example, a cord may be plugged into the electrical port and also plugged into the ultrasonic control console 128 to establish the communication link. The communication link may also be established wirelessly. The controller 204 may inform the ultrasonic control console 128 based on a type of tissue detected. The controller 204 may inform the ultrasonic control console 128 when target tissue is present or absent.

Based on the information provided from the controller 204, the ultrasonic control console 128 may adjust one or more operating parameters. For example, when target tissue is present, the resection rate may not be limited; however, when target tissue is not present, the resection rate may be limited such that the ultrasonic handpiece assembly 130 is prevented from cutting the healthy tissue. In such an example, the ultrasonic control console 128 may control the drive signal, such as the voltage, current, or both supplied to the ultrasonic handpiece assembly 130 based on the whether the target tissue is detected. While the example is provided that the controller 204 may communicate with the ultrasonic control console 128, the controller 204 may communicate with other surgical devices such as the surgical control console 115 to control the various surgical tools (e.g., bipolar forceps 160, neuro stimulators, dissectors, ablation devices, etc.) based on the absence or presence of target tissue.

With general reference to FIGS. 8-23, a detailed description of the sample probe 164 will follow. The sample probe 164 may include the fiber(s) 260, 264, 268, a compliance member 272, a connector 299, and optionally, a jacket 292. The fiber(s) 260, 264, 268 may be coupled between the connector 299 and a distal end 358 of sample probe 164. The distal end 358 of the sample probe 164 may include a lens or other optical component to allow for the collection and passage of light to and from the target tissue. The jacket 292 may enclose the fibers 260, 264, 268 in order to provide protection and shield the fiber(s) 260, 264, 268 from the environment. The jacket 292 may be formed with any suitable material including Polyethylene, Polyvinyl Chloride, Polyvinyl Difluoride, etc. The outer surface of the jacket 292 may be hydrophilic. A portion of the outer surface of the jacket 292 may also have small serrations such as to increase grip between the jacket 292 and whatever surface it comes into contact with. In some examples, a portion of the optical fiber may be coupled to one of the electrical cable(s) or suction lines of the surgical tools (i.e., the bipolar forceps 160, the ultrasonic handpiece assembly 130, or the suction tool 156), and a second portion of the fiber may be decoupled from the surgical tool. This allows the probe to rest in position while the user moves the surgical tool to perform surgery, such as resect tissue.

Figure 8:
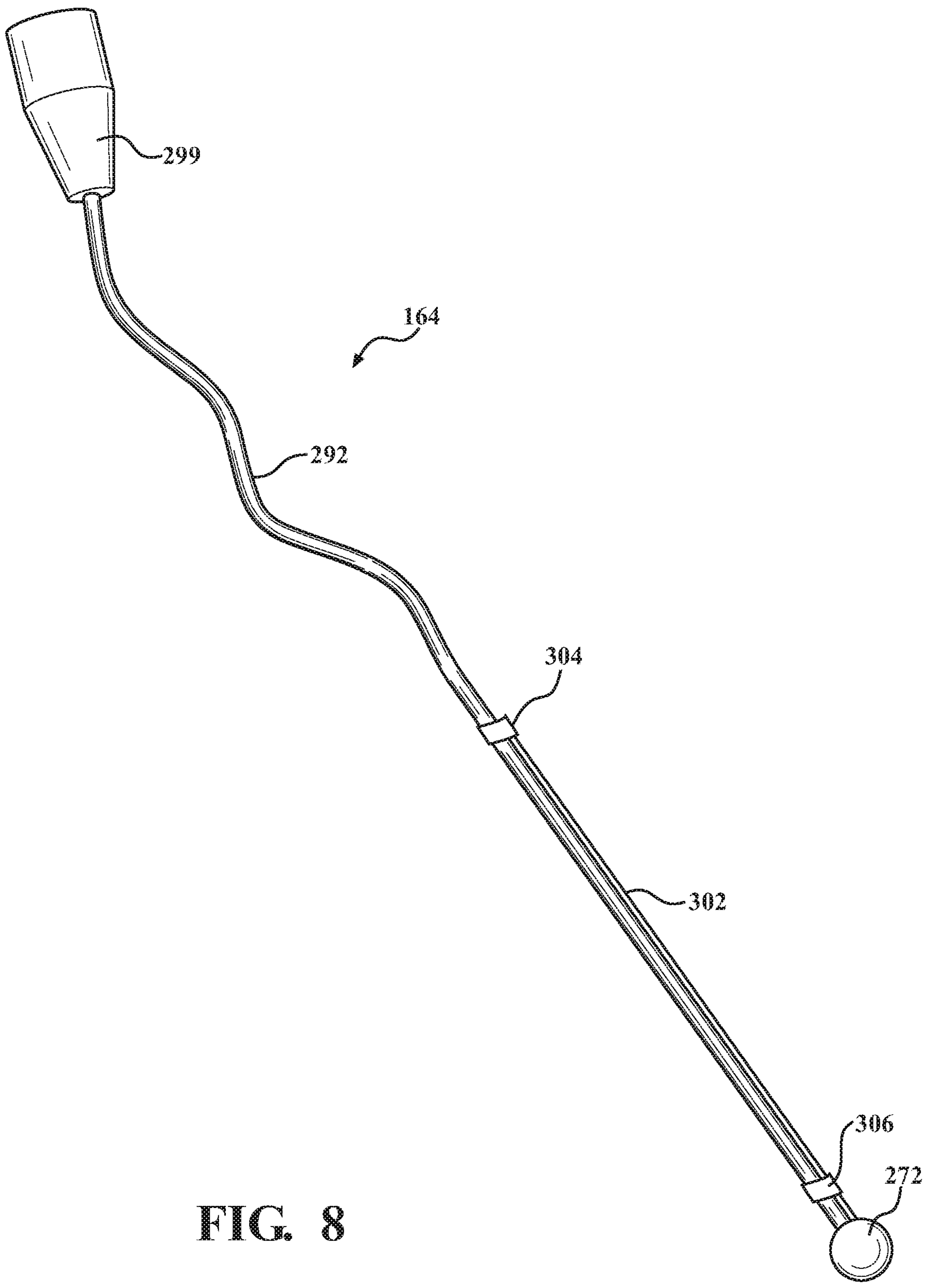
FIG. 8 depicts a sample probe of a tissue detection system, the sample probe including a carrier according to the teachings of the present disclosure.

With reference to FIG. 8, a carrier may be coupled to at least a portion of the jacket 292. The carrier may be configured to assume different shapes which in turns controls the shape of the portion of the jacket 292 in which the carrier is coupled to. The carrier may be a wire 302 or other malleable component including a first attachment portion 304 configured to attach to a first portion of the jacket 292 and a second attachment portion 306 configured to attached to a second portion of the jacket 292. The wire 302 may be attached between the first attachment portion 304 and the second attachment portion 306. The healthcare professional may bend the wire 302 or malleable member as desired in order to fix the shape of the relevant portion of the jacket 292.

In another example, the carrier may include a tension adjustment mechanism. The tension adjustment mechanism may be configured to adjust an amount of tension applied to the jacket 292. The tension adjustment member includes a first adjustment member, a second adjustment member and a flexible cable. The first adjustment member may be coupled to the compliance member and a first portion of the jacket 292. The second adjustment member coupled to a second portion of the jacket 292. The flexible cable may be connected between the first adjustment member and the second adjustment member. The second adjustment member may be configured to slidably move along the jacket 292 and in order adjust an amount of tension applied to the jacket 292. When the second adjustment member is at a first position, the second adjustment member is closer to the compliance member 272 than it is in a second position. In the first position, the flexible cable may be in a non-stiff state and the sample probe 164 may move freely as if there were no tension adjustment mechanism constraining movement. When the second adjustment member is in the second position, the flexible cable may be in a stiff state and the tension in the flexible cable constrains the movement of the portion of the jacket 292 coupled between the first and the second adjustment members.

Figure 9:
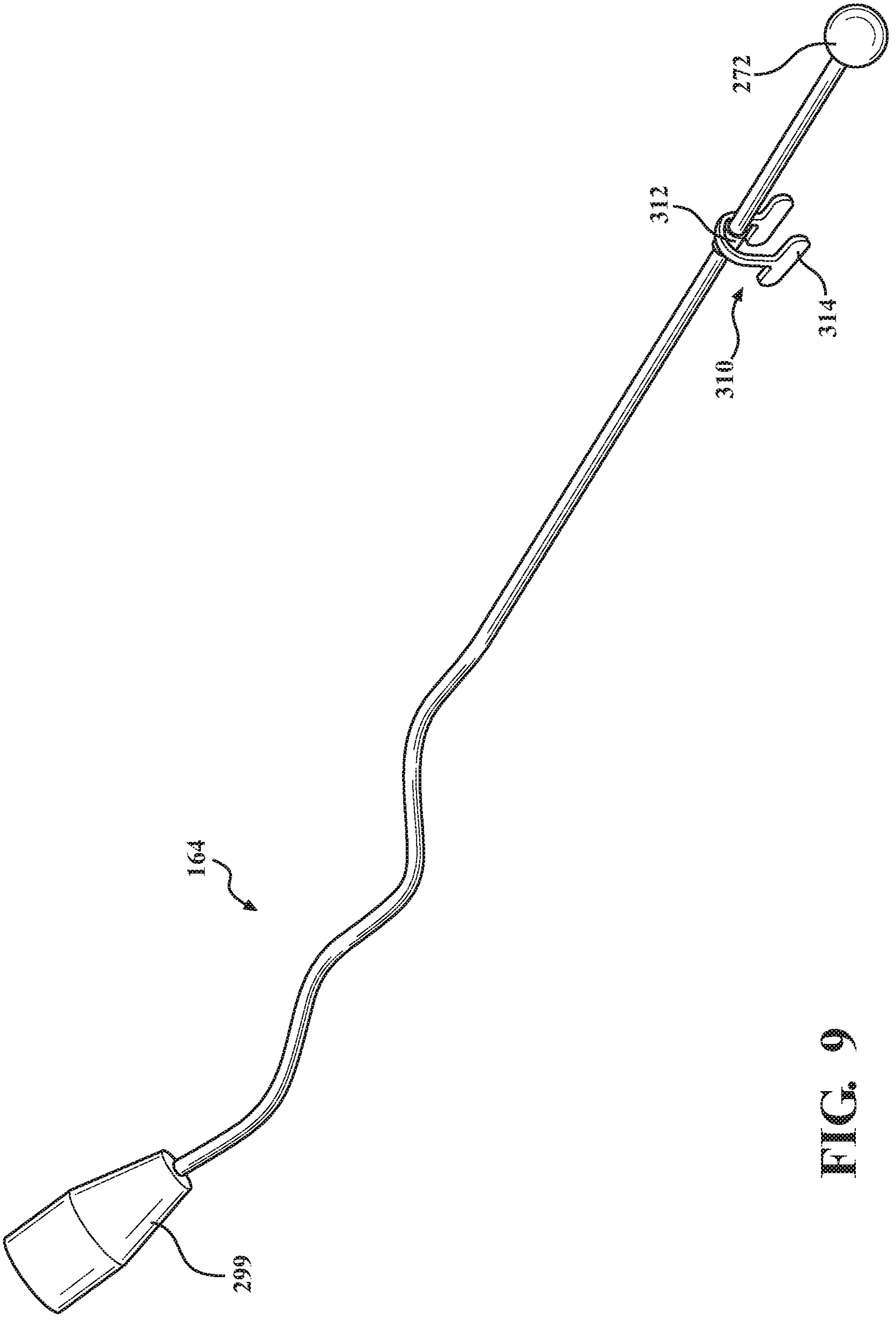
FIG. 9 depicts a sample probe of a tissue detection system, the sample probe including a clip according to the teachings of the present disclosure.

With reference to FIG. 9, a gripping element 310 may be removably coupled to the jacket 292 proximal to the compliance member 272. Thus, the gripping element 310 may be located proximal to the compliance member. The gripping element 310 may be implemented as a fastener configured to attach to a portion of the patient in order to prevent movement of the sample probe 164 from a desired position. The gripping element 310 may include a jacket attachment portion 312 and a patient engagement portion 314. The jacket attachment portion 312 may include a tubular like sleeve having a snug fit and configured to slide along the jacket 292 with application of force by a healthcare professional. The patient engagement portion 314 may be mounted or otherwise attached to the jacket attachment portion 312. The patient engagement portion 314 may include a clip or a clamp configured to be attached to the patient or inanimate component near the patient.

Figure 10:
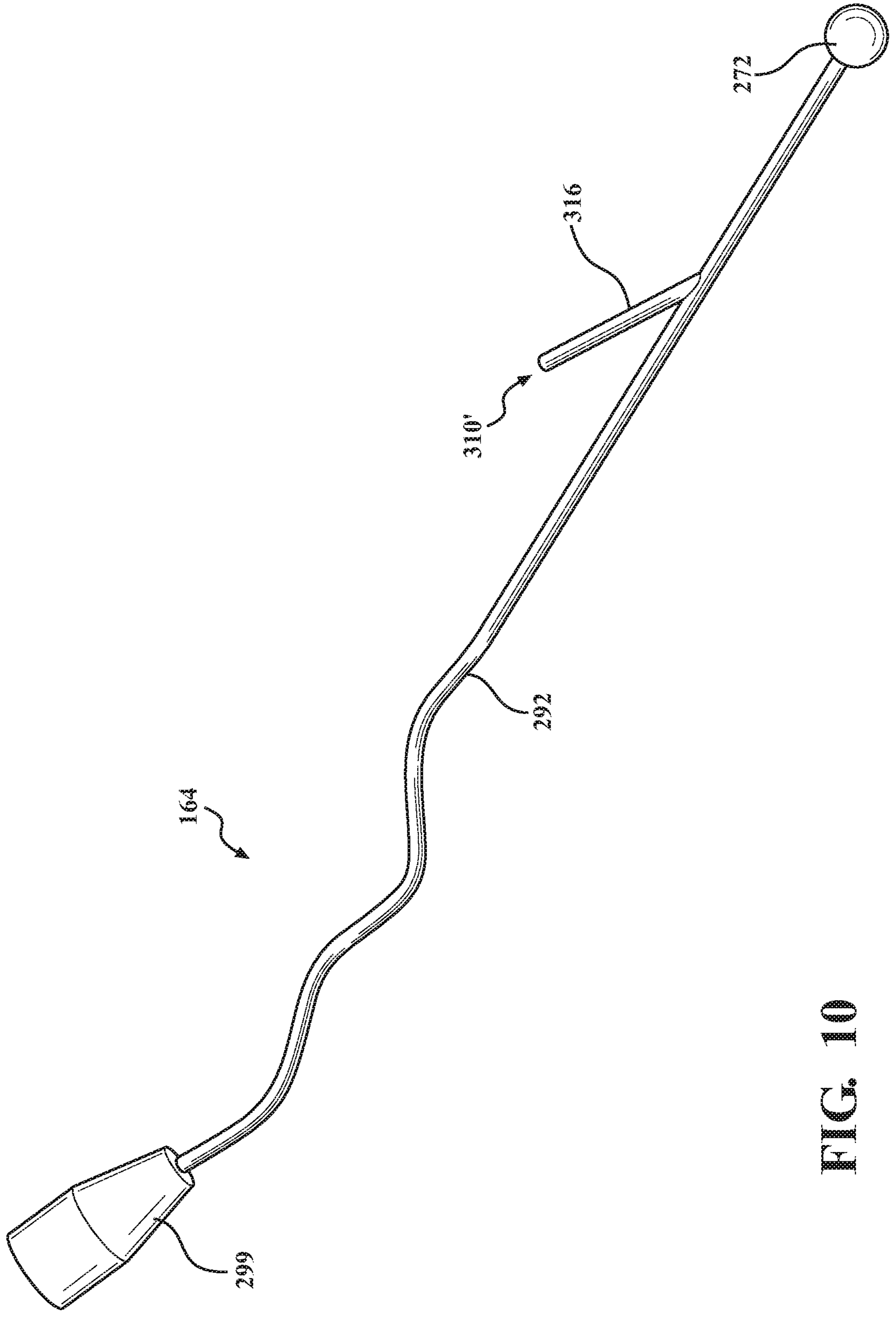
FIG. 10 depicts a sample probe of a tissue detection system, the sample probe including a projection according to the teachings of the present disclosure.

With reference to FIG. 10, the gripping element 310' may also be implemented as a tab 316 configured for engagement by the surgical tool. As an alternative to the tab, the compliance member may define a tubular like structure including a hole, aperture, or cavity slightly larger in diameter than the lumen of the suction tool 156 such that the suction tool 156 may be inserted through. The suction tool 156 may engage the tab 316 such as to guide the compliance member 272 into a hard to reach portion of the brain such as a deep narrow cavity of the brain.

Alternative, the compliance member may be free of any tab or gripping element, but may include a magnetic or ferrous material such that the compliance member can be maneuvered by use of a surgical tool that includes a ferrous metal or a magnetic material, respectively.

Figure 11:
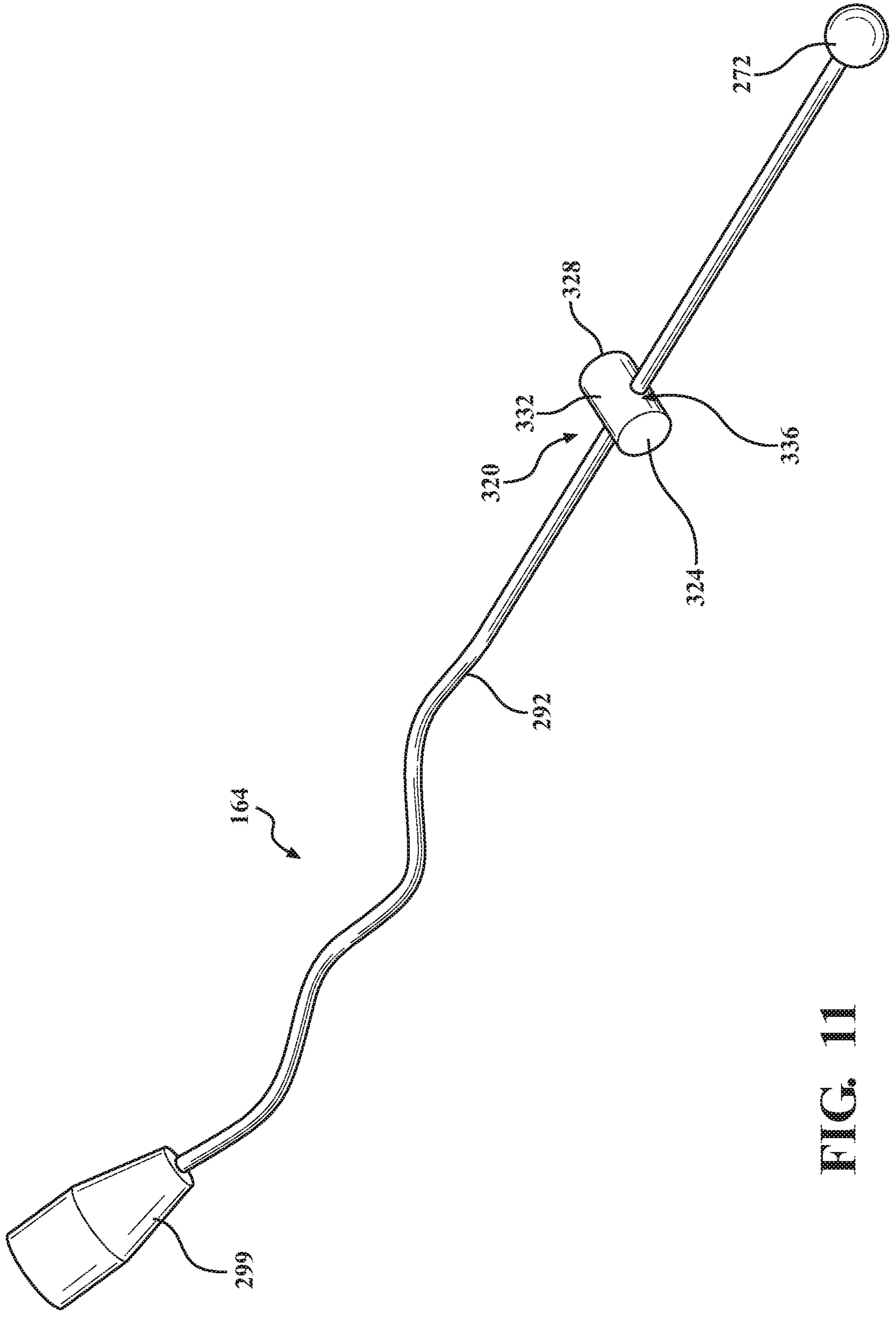
FIG. 11 depicts a sample probe of a tissue detection system, the sample probe including an anchor according to the teachings of the present disclosure.
Figure 12:
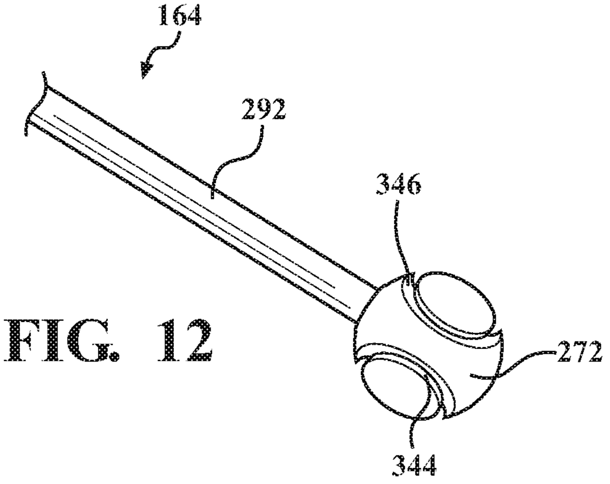
FIG. 12 depicts a sample probe of a tissue detection system, the sample probe including a compliance member having a plurality of ridges according to the teachings of the present disclosure.

With reference to FIG. 11, an anchor 320 may be coupled to the jacket 292 or fiber(s) and slidable along the length of the jacket 292. The healthcare professional may place the anchor 320 at any position along the length of the jacket 292 in order to anchor the sample probe 164 to a point of interest. The point of interest may correspond to a point of transition between the sterile field and non-sterile field, such as out of the patient or contacting skin or bone, as opposed to brain tissue. The anchor 320 may be cylindrical shaped. As such, the anchor 320 may include two-base ends 324, 328 connected by a curved surface 332. The curved surface 332 may be formed with a through bore 336 in which the sample probe 164 is inserted through. The anchor 320 may be formed of metal or another suitable dense material capable of countering the weight of the sample probe 164 and anchoring the sample probe 164 to a particular point of interest.

With additional reference to FIGS. 12-17, the compliance member 272 may be removably coupled to the jacket 292 and/or fibers at the distal end of the sample probe 164. In some implementations, the compliance member 272 is removable from the sample probe 164 so that a healthcare professional may reach a deep narrow cavity of the brain in which the sample probe 164 would not otherwise be able to reach with the compliance member 272 attached.

The compliance member 272 may be at least partially translucent to visible light and in some implementations, configured to deform in response to engagement by a surgical tool, such as the bipolar forceps 160, the suction tool 156, or the ultrasonic handpiece assembly 130. The compliance member 272 may be formed with any suitable material that is deformable, electrically insulating, and thermally insulating.

The material of the compliance member 272 may be selected to be refractive index-matching. Stated differently, the material of the compliance member 272 may be selected such that a refractive index of the compliance member 272 is within a predetermined threshold of a refractive index of the tissue and/or a refraction index of the fibers 264, 268 so that the refraction of light passing between the fiber(s) 264, 268 and the tissue is minimized. The collection fiber 268 may have a refraction index with a range of approximately 1.5 to 1.6, the compliance member 272 may have a refraction index of approximately 1.45, and the tissue may have a refractive index varying approximately between 1.395 to 1.410.

The material of the compliance member 272 may be selected based on other desired optical properties for the compliance member 272 such as the ability to disperse light from the excitation fiber 264 and/or indication fiber 260 broadly to the surrounding environment. The compliance member may be formed of a polymer. In certain embodiments, the compliance member may be a foam. The compliance member may comprise a bioresorbable material, such as a polyurethane. Bioresorbable refers to the ability of being completely metabolized by the human or animal body. The compliance member may be formed from a material selected from silicone, polyvinylchloride, a hydrogel, a polyurethane, a polysaccharide, cellulose, polylactic acid, and combinations thereof. The compliance member may have has a Rockwell Shore Hardness 00 of 10-50, 10-40, or 10-30 or a Rockwell Shore Hardness A of 0-20, or 0-10.

The compliance member 272 may be sphere shaped. Optionally, with the sphere-shaped configuration, the compliance member 272 may include an aperture that may expose a portion of the distal end of the sample probe 164 to the environment. The compliance member 272 may have a smooth surface or may include one or more features on the outer surface that make it easier for a surgical tool, such as the bipolar forceps 160 or the suction tool 156, to engage the compliance member 272. For example, with reference to FIG. 12, the one or more features may include a plurality of ridges including a first ridge 344 and a second ridge 346 extending along an outer surface. The bipolar forceps 160 may engage the compliance member 272 at either of the first ridge 344 or the second ridge 346 using the tines so that the compliance member 272 does not slip out from the grip of the bipolar forceps 160 or any other surgical tool.

While the compliance member is described as being compliant in several aspects of this disclosure, in some implementations, the compliance member may be not be compliant or deformable, and in this instances, the compliance member may be referred to as a locating member, where the locating member may include any of the features described above with respect to the compliance member, but for the ability to deform in response to engagement by the surgical tool.

Figure 13:
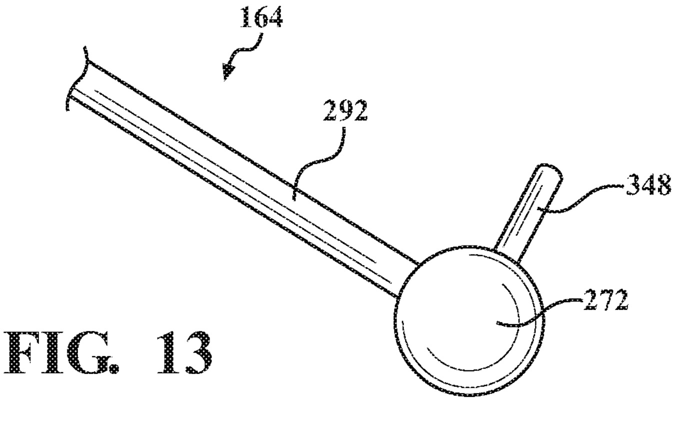
FIG. 13 depicts a sample probe of a tissue detection system, the sample probe including a compliance member having a projection according to the teachings of the present disclosure.

With reference to FIG. 13, the one or more features may include a projection 348. The projection 348 may extend along an axis transverse (or at any angle) relative to an axis of at least one of the collection fiber 268 and/or the excitation fiber 264. The projection 348 may be sized to be disposed at least partially within a lumen of the suction tool 156 or the ultrasonic handpiece assembly 130. Thus, suction may be applied with the suction tool 156 when the projection 348 is disposed within the lumen and the healthcare professional may move the compliance member 272 to a desired location. The projection is optional, and need not be included in all configurations of the probe. The projection may extend from an outer surface of the compliance member, and may optionally be integral with the compliance member. The projection may be included with the locating member implementation.

Figure 14:
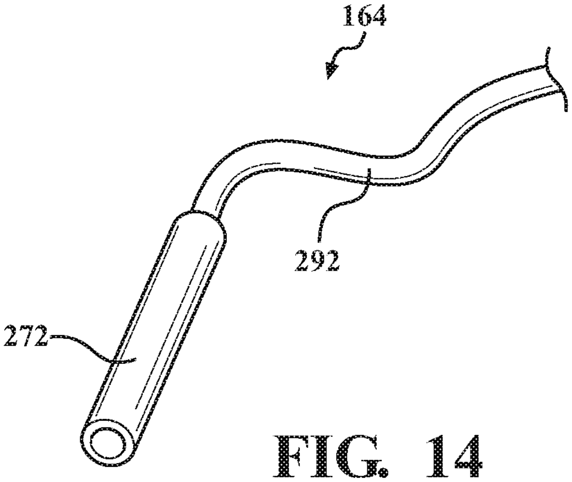
FIG. 14 depicts a sample probe of a tissue detection system, the sample probe including a compliance member having a cylindrical shape according to the teachings of the present disclosure.

A shown in previous FIGS., the compliance member 272 is shown to have the shape of a sphere but it is understood that the compliance member 272 may take on any shape. As shown in FIGS. 14-17, the compliance member 272 may be tubular shaped as shown in FIG. 14, cone shaped as shown in FIG. 15, rectangular or cube-shaped as shown in FIG. 16, or as shown in FIG. 17, an invertible C-shape that allows for a distal portion of the compliance member 272 to be moved relative to a distal end of the sample probe 164 such that the sample probe 164 is able to illuminate the target area in a diffused mode or a focused mode, as discussed in greater detail in the preceding paragraph.

Figure 18A:
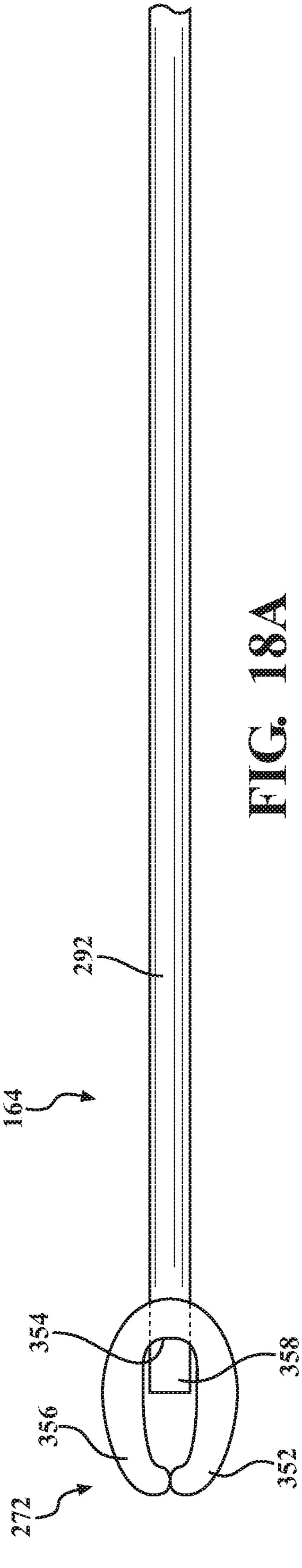
FIGS. 18A and 18B depict a sample probe of a tissue detection system, the sample probe having an invertible C-shape shown in a diffused position and a focused position according to the teachings of the present disclosure.
Figure 18B:
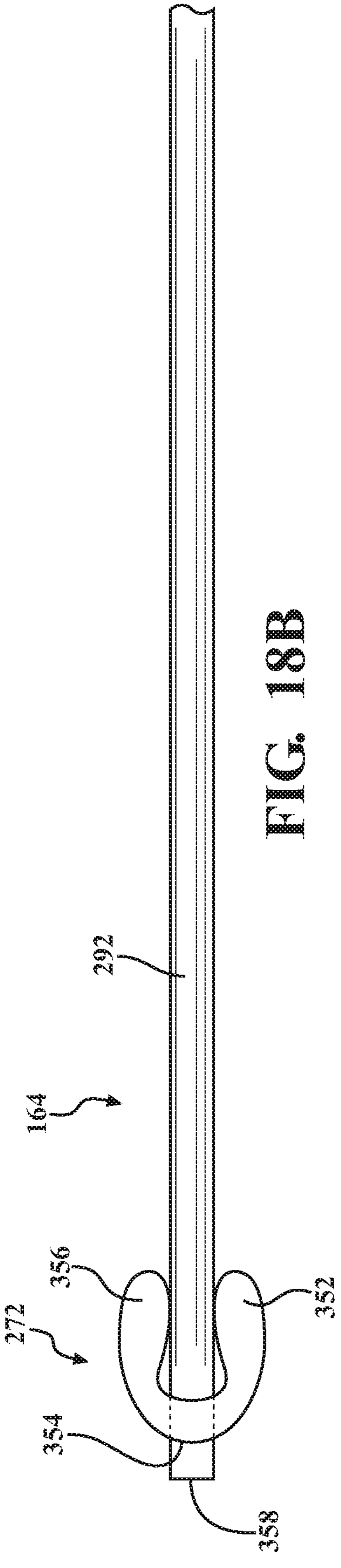

As shown in FIGS. 18A and 18B, the compliance member 272 may include a first portion 352, a center portion 354, and a second portion 356. The center portion 354 may include an aperture in which the distal end 358 of the sample probe 164 is inserted therethrough. In a diffused position, the first portion 352 and the second portion 356 may extend forward from the distal end 358 of the sample probe 164 such that the sample probe 164 delivers diffused excitation light (i.e., light hat spreads in all directions) to the target area. In a diffused position, at least a portion of the first portion 352 and at least a portion of the second portion 356 may be in contact with each other. In a focused position, the first portion 352 and the second portion 356 may be folded or peeled back by the health care professional such that the center portion 354 of the compliance member 272 is disposed forward the first portion 352 and the second portion 356 and closer to the distal end 358 of the sample probe 164. In the focused position, the distal end 358 of the sample probe 164 is exposed and configured to deliver focused excitation light (i.e., light that is directed straight out of the sample probe 164 and that may enter small target area) to the target area. It should be understood that in the diffused position, the excitation light is more diffused than in the focused position. Similarly, in the focused position, the excitation light is more focused than when in the diffused position.

Figure 19:
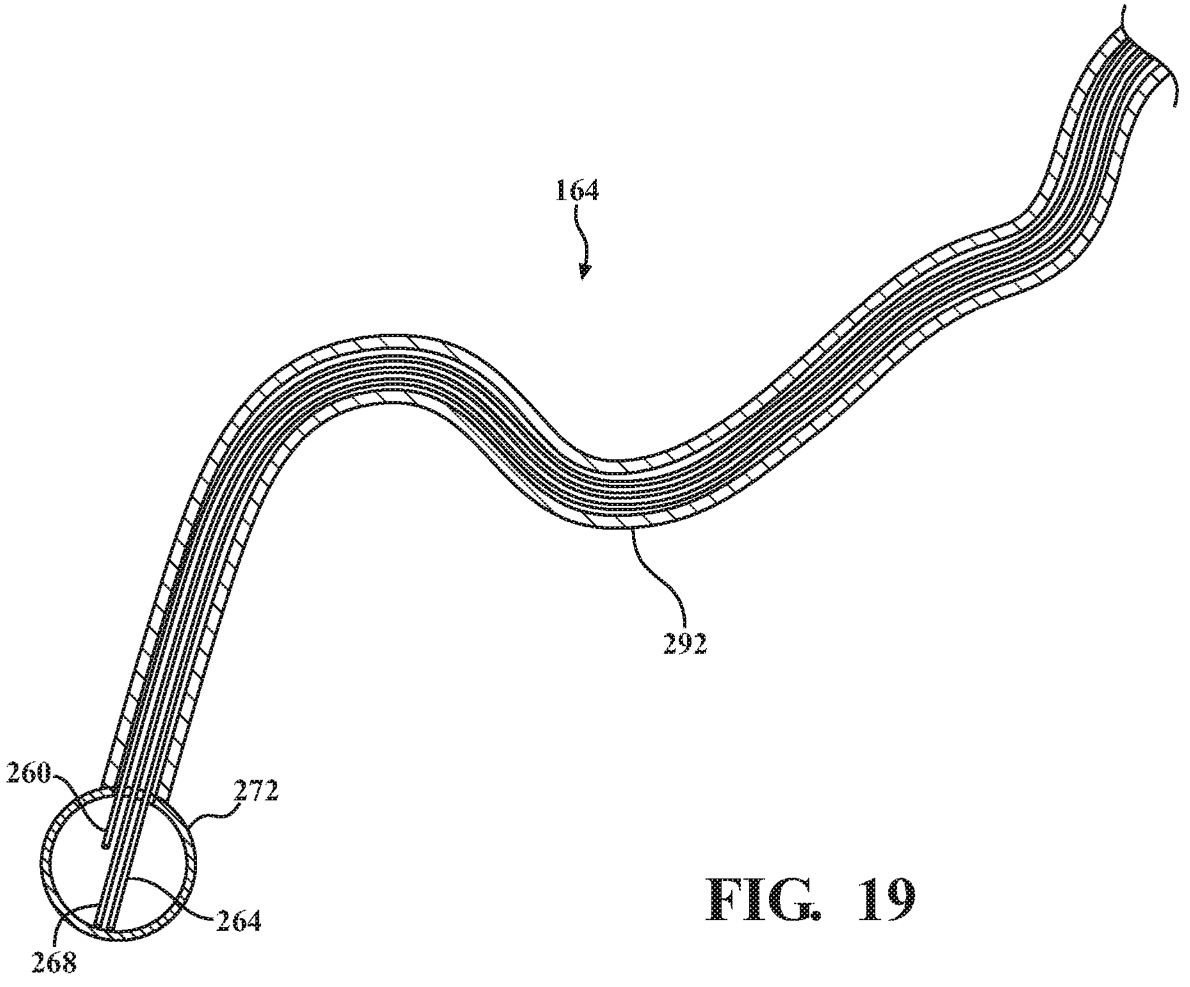
FIG. 19 depicts a cross-sectional area of a sample probe of a tissue detection system, the sample probe according to the teachings of the present disclosure.

With reference to FIG. 19, a cross section of one implementation of the sample probe 164 is shown. As described previously, the jacket 292 of the sample probe 164 may enclose the fibers 260, 264, 268 in order to provide protection and shield the fibers 260, 264, 268 from the environment. In some examples, the excitation fiber 264 and the collection fiber 268 may be disposed closer to the distal portion of the compliance member 272 or locating member than the indicator fiber 260. As discussed previously, the compliance member 272 may include an aperture at the distal portion which exposes the excitation fiber 264 and the collection fiber 268 to the environment such that the excitation fiber 264 is able to illuminate the target area with excitation light and the collection fiber 268 is able to collect light from the target area without the light traveling directly through the material that forms the compliance member/locating member. The compliance member 272 may include a first and second hemisphere with the excitation fiber 264 and collection fiber 268 being disposed in the first hemisphere and the indicator fiber 260 being disposed in the second hemisphere.

Figure 20:
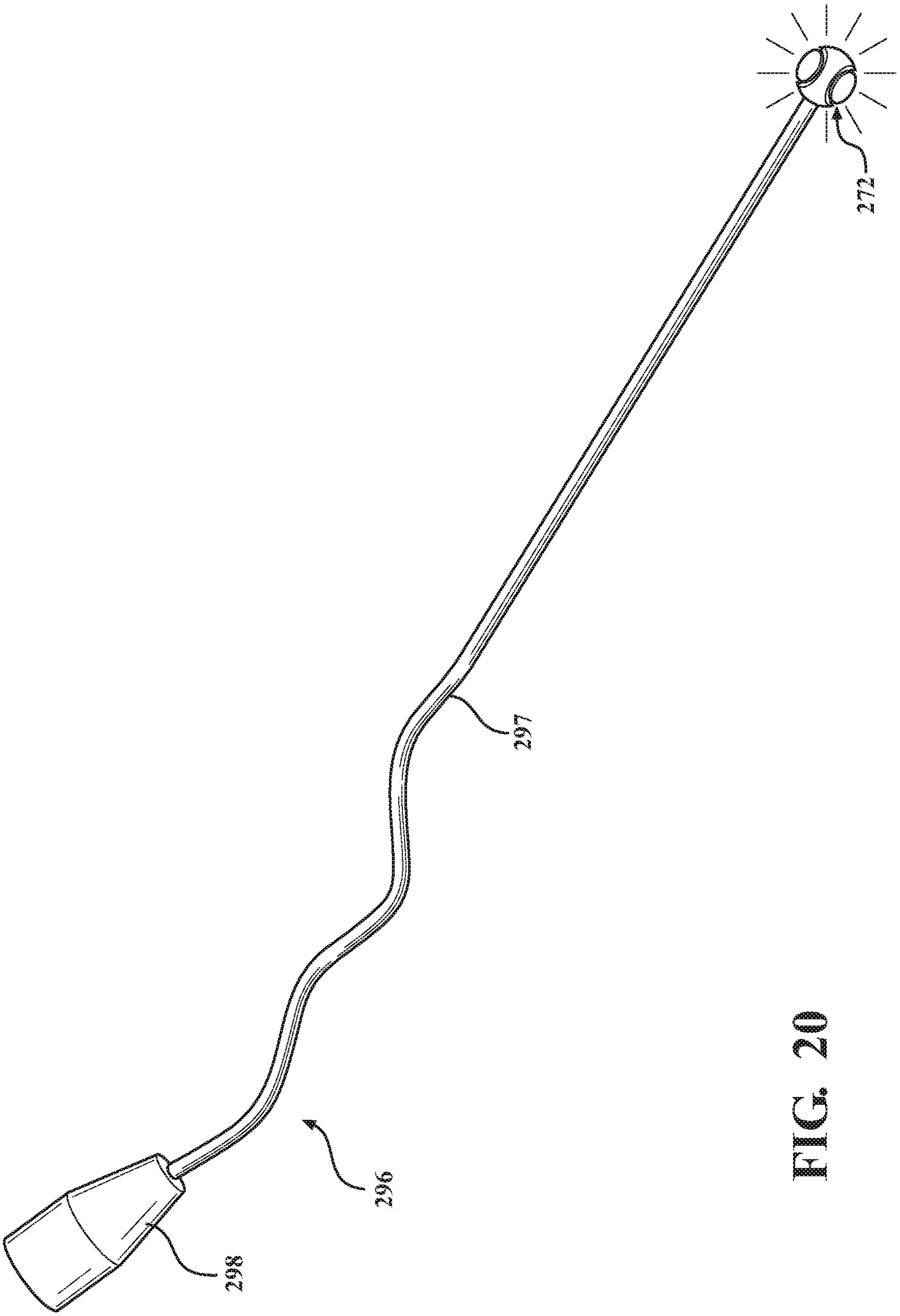
FIG. 20 depicts a sample probe of a tissue detection system, the sample probe including a compliance member in an illuminated stated according to the teachings of the present disclosure.
Figure 21:
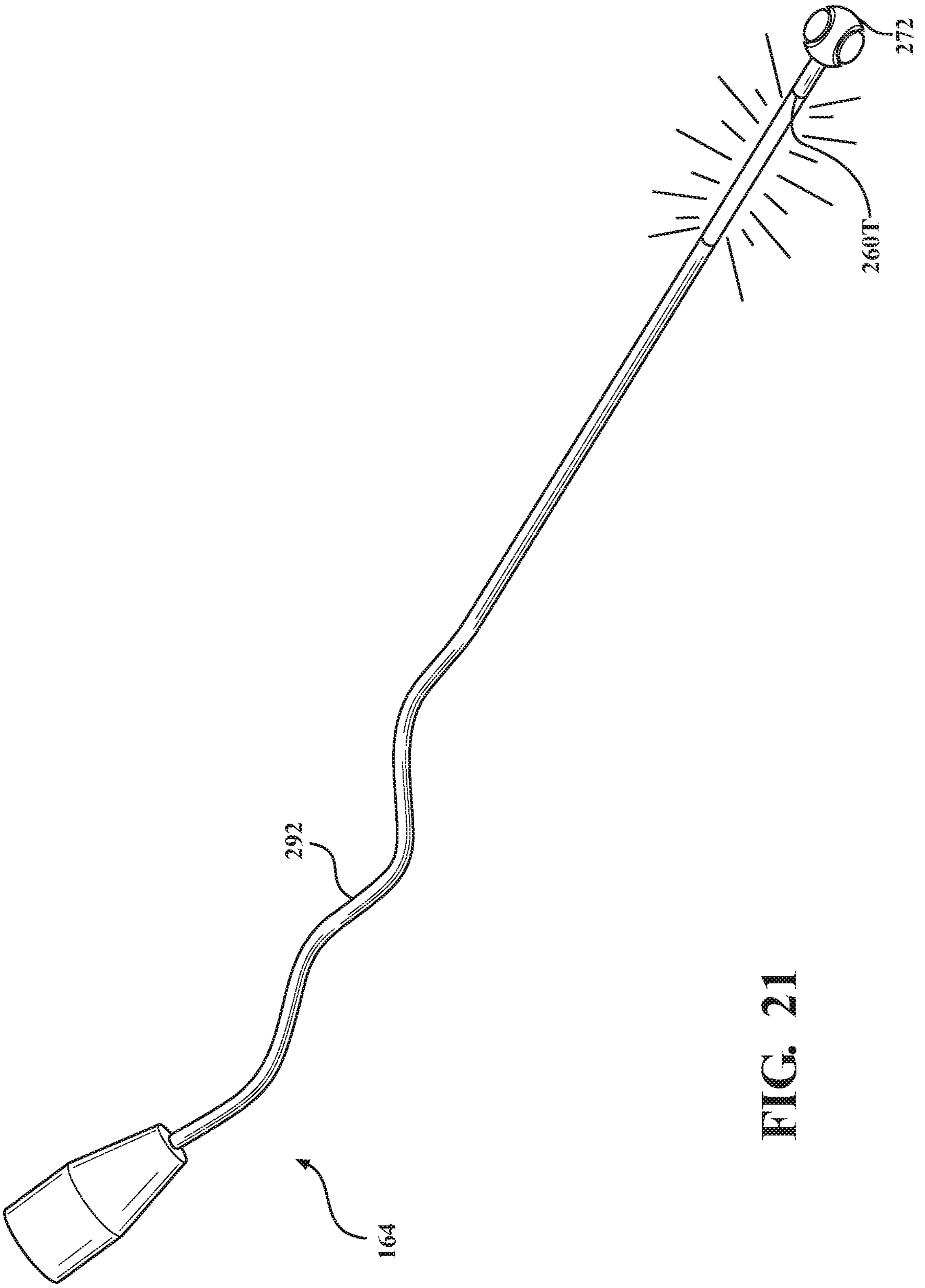
FIG. 21 depicts a sample probe of a tissue detection system, a portion of the sample probe being in an illuminated state according to the teachings of the present disclosure.

As shown in FIG. 20, when a tip of the indicator fiber 260 is disposed with the compliance member 272, the light from the indicator fiber 260 may light up the compliance member 272 to indicate the presence of the target tissue. However, in some examples, such as shown in FIGS. 21 and 22, the indicator fiber 260 is not disposed within the compliance member 272 at all and instead the indicator fiber 260 may illuminate another portion of the sample probe 164, and may terminate at a distal end 260T, which is outside of the compliance member.

Figure 22:
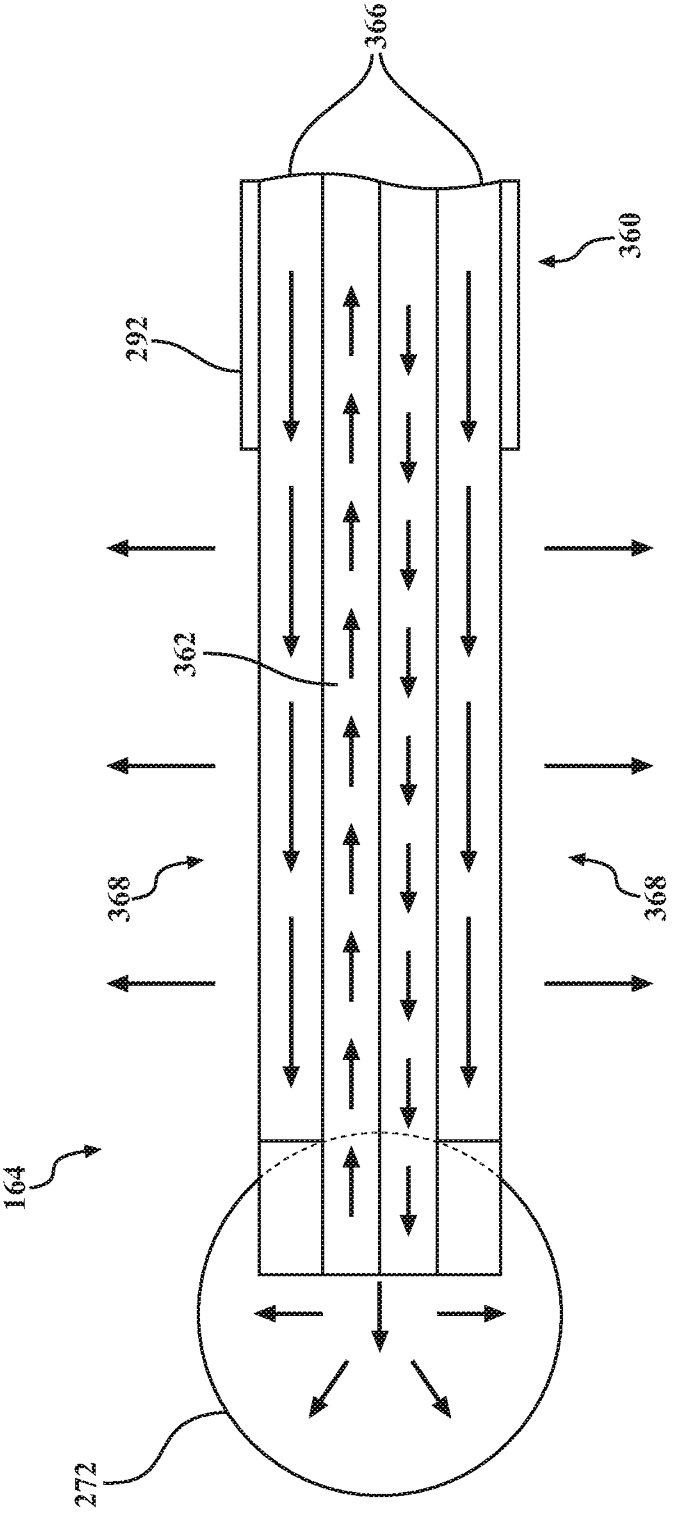
FIG. 22 depicts a sample probe of a tissue detection system, the sample probe including a co-axial fiber according to the teachings of the present disclosure.

In such an example, with reference to FIG. 22, the sample probe 164 may be a co-axial fiber 360 with a central core 362 and an outer channel 366. At least a portion of the sidewall of the outer channel 366 may be transparent. The excitation fiber 264 and the collection fiber 268 may be disposed within the central core 362 while the indicator fiber 260 is disposed within the outer channel 366. A distal portion of the central core 362 may be disposed within the compliance member 272. The indicator fiber 260 may emit light through the sidewalls of the outer channel 366. The sample probe 164 may have an exposed portion 368 in which the jacket 292 does not cover the entire length of the co-axial fiber 360 such that the light emitted through the side walls is visible to the healthcare professional via the exposed portion 368. The exposed portion 368 may be situated proximal to the compliance member 272 to ensure that the healthcare professional is able to view the indicator light emitted as the healthcare professional is resecting tissue. Optionally, the exposed portion 368 may be covered with a clear or transparent piece of plastic or another suitable material. As such, the side wall of the outer channel may be transparent and configured to allow the indicator element, such as an LED, to diffuse light to an ambient area.

In another example, as described above, the indicator fiber 260 may be omitted entirely. Instead, the sample probe 164 may include a light emitting diode (LED) that is activated in response to receiving the activation signal. The LED may be disposed proximal to the compliance member 272 and coupled to an outer surface of the jacket 292 or at another suitable location along the sample probe 164. In another example, others forms of indication may be provided such as an audible indication generated by a speaker associated with the control console 168 or a haptic indication generated by a haptic device attached to the sample probe 164. In other words, indicator form may take the form of a indicator element, such as a light source, and the indicator element need not take the form of a fiber, and the indicator element need not necessarily be disposed within or partially within the compliance member or locating member, but rather the indicator element could be positioned proximally or distally the compliance member, and alternatively, the indicator element may appear as an icon or display element on the console.

Figure 23:
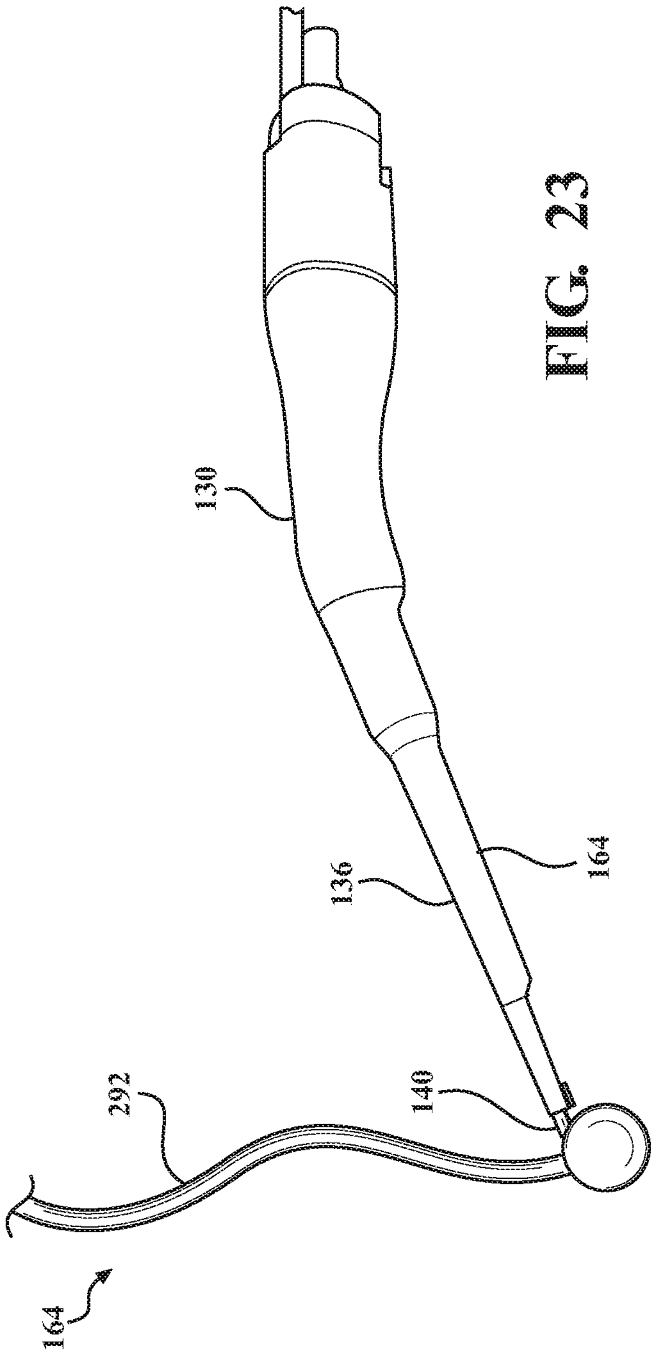
FIG. 23 depicts a sample probe of a tissue detection system being engaged by an ultrasonic handpiece assembly according to the teachings of the present disclosure.
Figure 24:
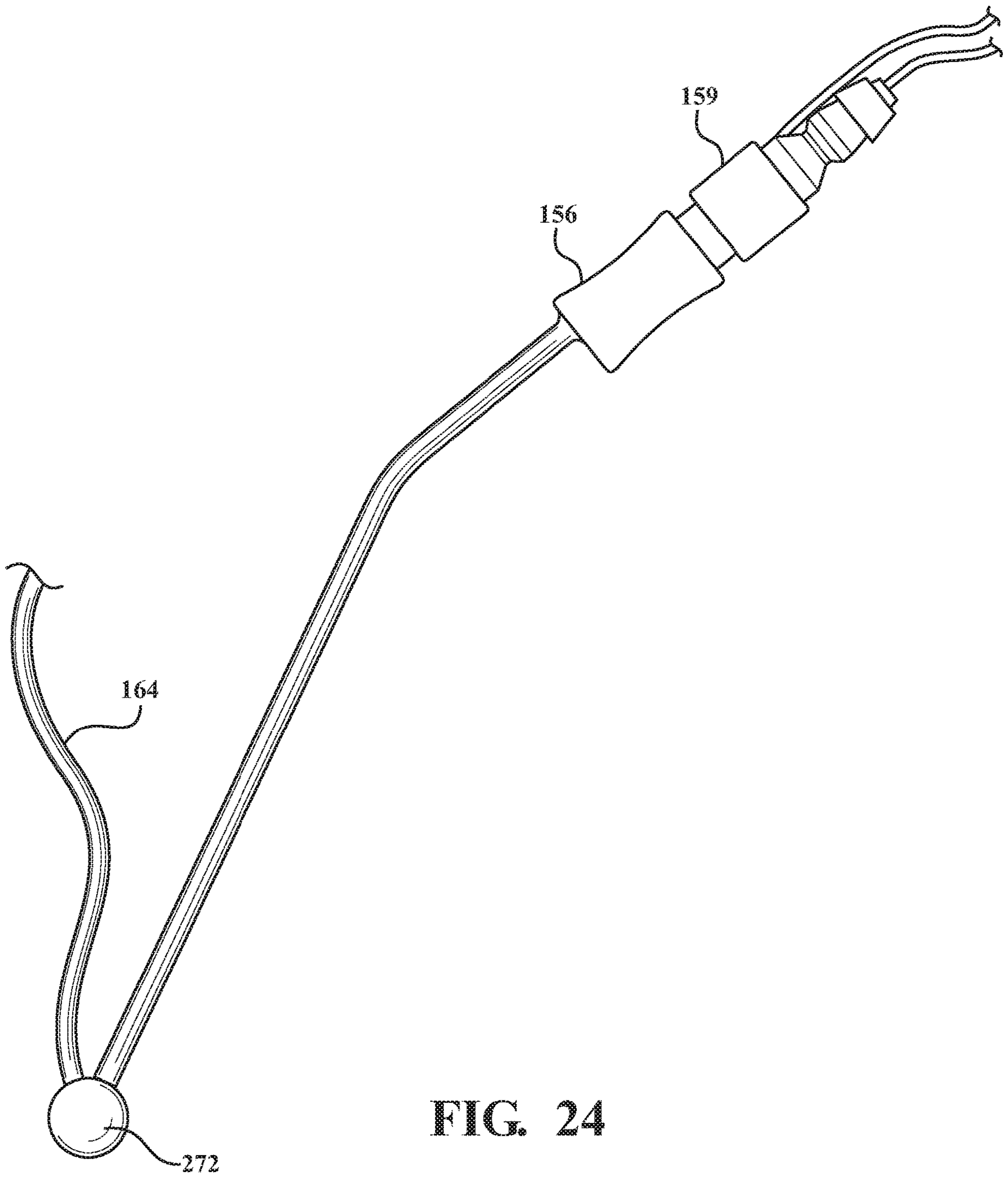
FIG. 24 depicts a sample probe of a tissue detection system being engaged by a suction tool according to the teachings of the present disclosure.
Figure 25:
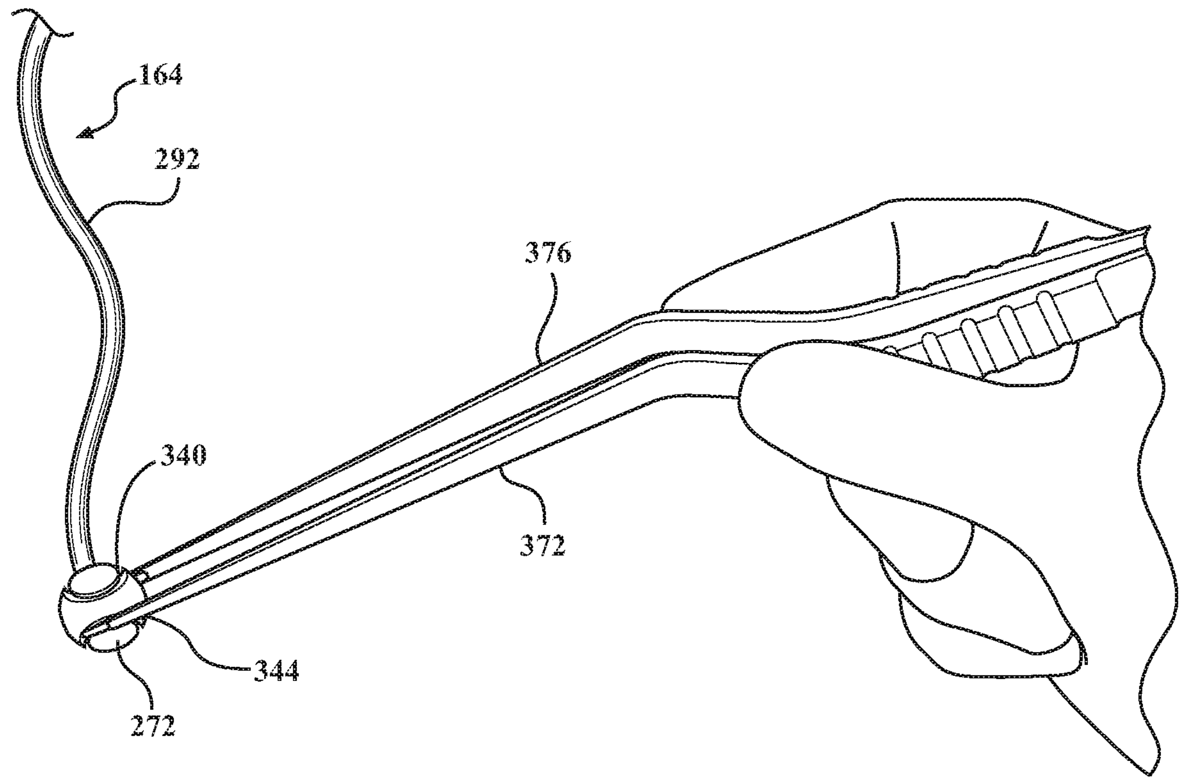
FIG. 25 depicts a sample probe of a tissue detection system being engaged by bipolar forceps according to the teachings of the present disclosure.

With reference to FIGS. 23-25, various surgical tools are shown engaging the sample probe 164. In FIGS. 23 and 24, either the ultrasonic handpiece assembly 130 or the suction tool 156 is directly engaging the compliance member 272; however, as previously described, the compliance member 272 may include the projection 348 (hidden from view as disposed in the lumen) which may fit into a lumen of the ultrasonic handpiece assembly 130 or the suction tool 156. Once the ultrasonic handpiece assembly 130 or the suction tool 156 is coupled to the compliance member 272, suction may be applied by the healthcare professional in order to move the compliance member 272 to a desired location. In FIG. 24, the compliance member 272 is engaged by the bipolar forceps 160, having tines 372, 376. As illustrated, the compliance member 272 includes the previously described plurality of ridges 340, 344. The compliance member 272 may be gripped by the bipolar forceps 160 at one or both of the plurality of ridges 340, 344.

A tracking system may be used and coupled to the navigation computer. The tracking system is configured to sense the pose (i.e., position and orientation) of one or more tracking elements attached to probe and provide the pose to the navigation computer. The tracking elements may be active or passive infrared tracking elements. An example of a surgical navigation system 104 which includes a tracking system is Nav3i™ that is commercially available from Stryker. A surgical navigation system 104 may have various functions and features as described in U.S. Pat. No. 7,725,162 B2 and U.S. Pat. Pub. No. 2020/0100849 A1 which are hereby incorporated by reference in their entireties.

Figure 26:
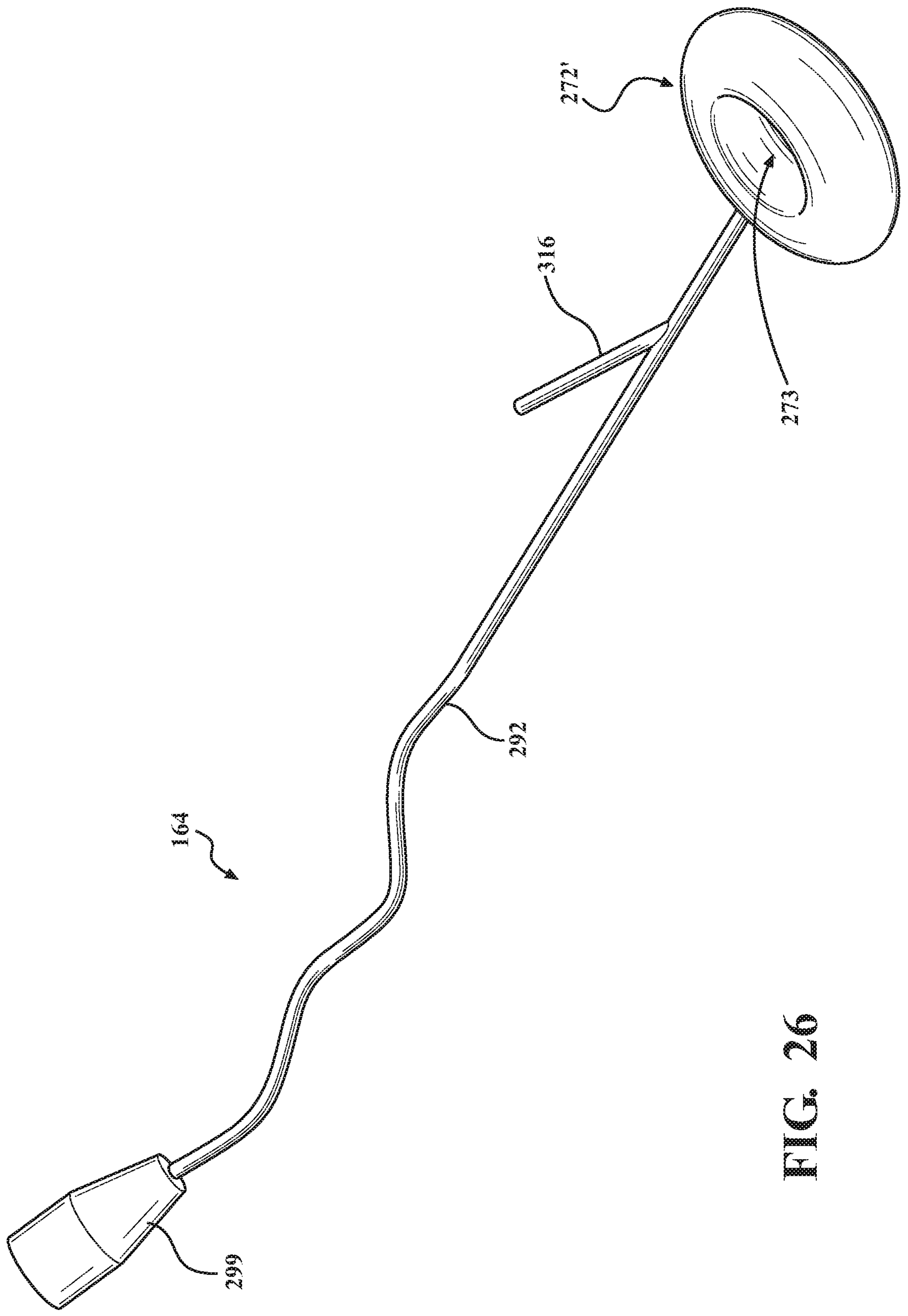
FIG. 26 depicts a sample probe of a tissue detection system defining a lumen.

Referring now to FIG. 26, the member 272', such as the compliance member, defines a lumen 273. This may allow the user to position surgical tools therethrough. In this configuration, the compliance member 272' may be coupled to the optical fibers as described throughout. The compliance member 272' may assume the shape of a doughnut or a cylindrical shape. The indicator may be disposed within the compliance member 272' as described above, such as an LED or the distal end of the indicator fiber may be disposed within the compliance member 272'. The lumen may be sized to allow a portion of the surgical tool to be placed therethrough. The lumen may range in size, but is at least 0.5 cm in diameter, or ranging from 0.3 cm to 1.5 cm in diameter.

Figure 27A:
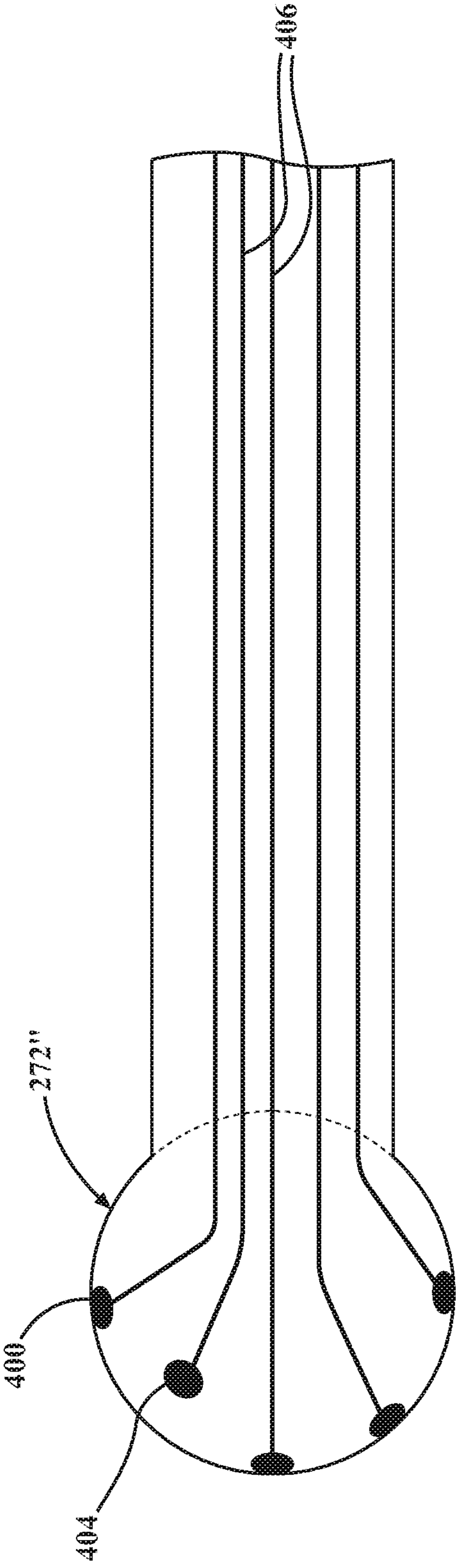
FIGS. 27A & 27B depict a sample probe of a tissue detection system that includes one or more electrodes for providing stimulation and/or receiving electrical signals from the brain.
Figure 27B:
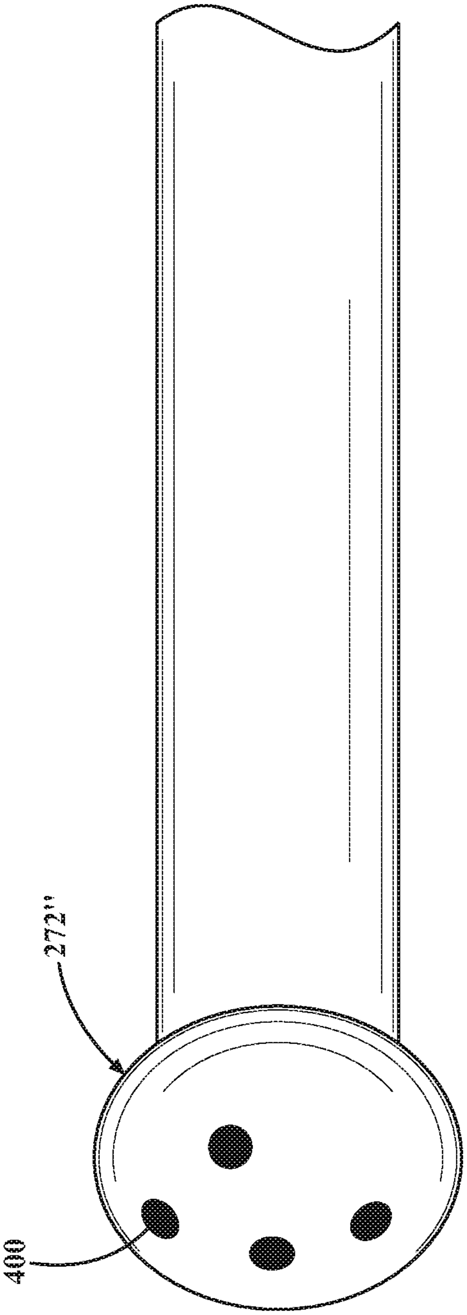

Referring to FIGS. 27A and 27B, the locating member 272" includes one or more electrodes 400 positioned on the surface of the member 272". The locating member may be the compliance member described throughout but may optionally omit the optical fibers for optical detection. The electrodes 400 may be spaced apart from one another such that they can be in contact with tissue that abuts the circumference or outer surface of the member 272". The electrodes 400 may be coupled to a detection module that processes the electrical signals received by the electrode(s) to determine a tissue type, such as whether the tissue contacted by the electrode is a critical structure. For example, the electrodes may facilitate functional mapping, bioimpedance analysis, or other electrical analysis of the brain tissue. The detection module may be coupled to an indicator 404, such as an LED or an optical fiber. In instances where the indicator is an LED or other light source, the member 272" may include a conductor 406. The indicator 404 may illuminate when a target tissue is detected, such as lighting red when a critical tissue type has been detected, and lighting green when a non-critical tissue type has been detected. Exemplary processing techniques and electrode constructions can be found in U.S. Pat. Nos. 8,442,653 and 10,918,857 and U.S. Patent Pub. No. 20080027346, which are hereby incorporated by reference in their entirety. Exemplary techniques include functional brain mapping, electroencephalography, magnetoencephalography, electrocorticography, or combinations thereof. The probe may be placed such that the electrode is placed on a particular region of the brain and/or on, through or inside of intracranial or extracranial blood vessels or other tissues at a second position not in contact with said particular region of the brain but electrically coupled to the brain, and monitoring the brain activity from said particular region through signals received by the electrode.

Figure 28:
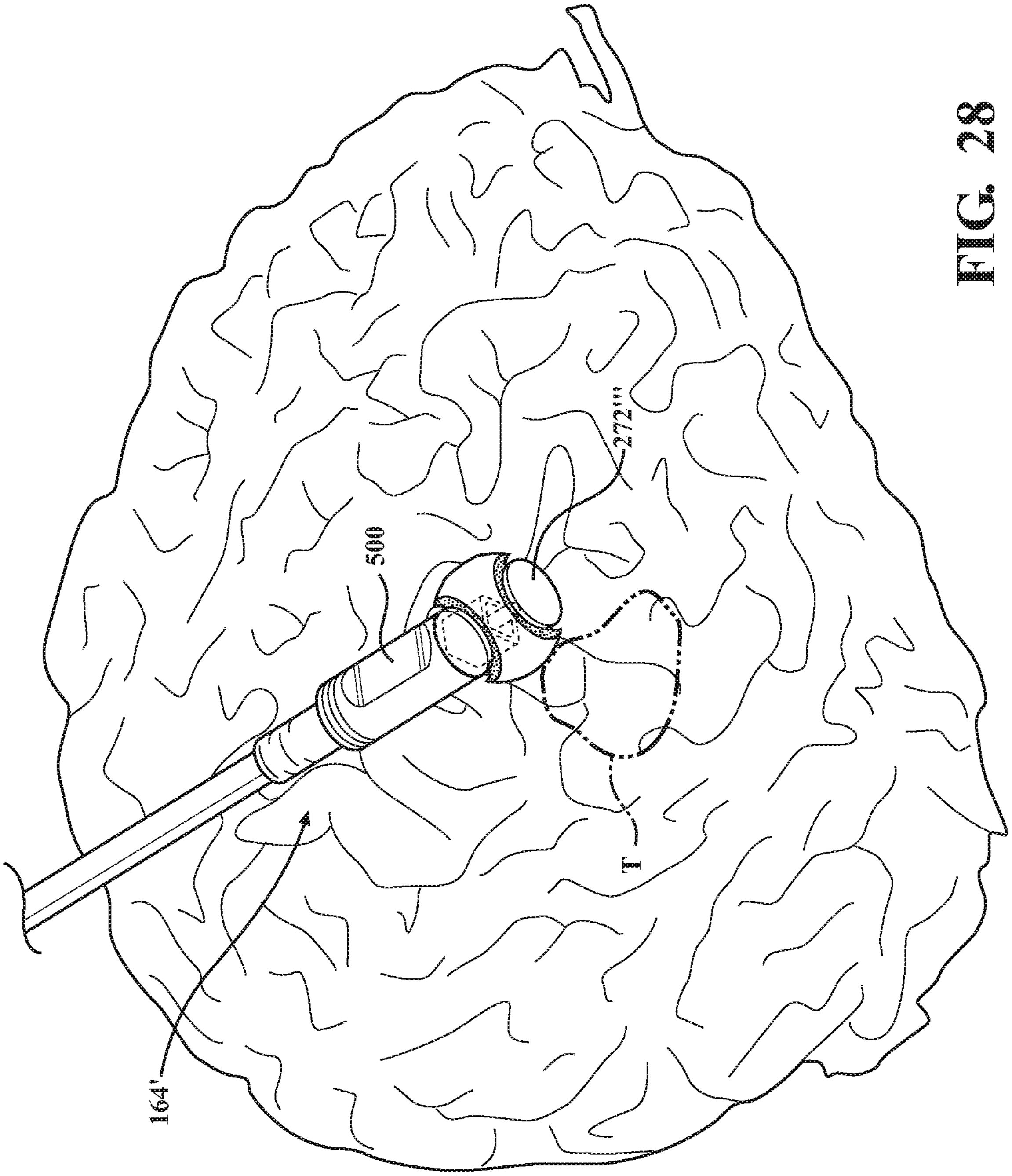
FIG. 28 depicts a sample probe of a tissue detection system that includes a connector allowing the probe to be disconnected from the compliance member at a surgical site and the compliance member imaged with a scanner.

Referring to FIG. 28, the probe 164' may include a connector 500 that allows the compliance member 272"" to be detached from the fiber and/or conductor and remain at the surgical site. In such an implementation, the compliance member 272''' may include radiopaque material. During use of the probe, the compliance member 272''' may be detached from the probe and the surgical site may be imaged using an imager, such as an MRI scanner or CT scanner. The incorporation of radio-opaque material into the compliance member 272''' allows the compliance member to be visualized relative to other critical structures. It is contemplated that the radiopaque material be gadolinium, but other radiopaque materials are also contemplated. It is also contemplated that only a portion of the compliance member be removed from the probe, and this removed portion contain the radiopaque material and be visualized with the imager. The radiopaque material may be dispersed in the compliance member, or may be received in a pocket.

International Application No. PCT/IB2022/052294, is hereby incorporated by reference in its entirety, and aspects may be used in conjunction with the probe described herein.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including “connected,” “engaged,” “coupled,” “adjacent,” “next to,” “on top of,” “above,” “below,” and “disposed.” Unless explicitly described as being “direct,” when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean “at least one of A, at least one of B, and at least one of C.” The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term “controller” or “module” may be replaced with the term “circuit.” The term “controller” may refer to, be part of, or include: an Application Specific Integrated Circuit (ASIC); a programmable system on a chip (PSoC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits with one or more transceivers. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system may include physical and/or virtual networking equipment such as hubs, switches, routers, gateways and transceivers. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called “Verilog”) and IEEE Standard 1076-2008 (commonly called “VHDL”). The hardware description language may be used to manufacture and/or program a hardware circuit. In some implementations, some or all features of a controller may be defined by a language, such as IEEE 1666-2005 (commonly called “SystemC”), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above may serve as software specifications, which can be translated into the computer programs by the routine work of a skilled technician or programmer. The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Clauses for Additional Protection:

I. An optical sensor system for detecting a tissue type in a surgical procedure, the optical sensor system comprising: an excitation source configured to selectively emit excitation light; a probe comprising: at least one fiber coupled to the excitation source and configured to illuminate target tissue with excitation light and collect light from target tissue; a compliance member coupled to the at least one fiber, the compliance member being at least partially translucent and configured to deform in response to engagement by a surgical tool, wherein a portion of the at least one fiber is disposed inside of the compliance member; an indicator configured to provide an indication in response to receiving an indicator signal; an optical detection module coupled to the at least one fiber and configured to generate a signal based on the collected light; and a controller operatively connected to the optical detection module and configured to determine a tissue characteristic based on the signal and generate the indicator signal based on the determined tissue characteristic.

II. The optical sensor system of clause I, further comprising an indicator fiber, wherein the excitation source is further defined as a first excitation source, wherein the indicator includes a second excitation source coupled to the indicator fiber and the indication includes light generated by the second excitation source in response in response to receiving the indicator signal.

III. The optical sensor system of clause I, wherein the indicator includes a light emitting diode (LED) which is activated in response to receiving the indicator signal.

IV. The optical sensor system of clause I, wherein the indicator includes a speaker and the indication includes an audible sound generated by the speaker in response in response to receiving the indicator signal.

V. The optical sensor system of clause II, wherein the indicator is a haptic device configured to be coupled to at least one of a surgical tool and the at least one fiber, wherein the indication is in the form of haptic feedback generated by the haptic device in response to receiving the indicator signal.

VI. An attachment for an optical probe including at least one fiber configured to illuminate target tissue with excitation light and collect fluorescent light from the target tissue, the optical probe further comprising an indicator element configured to emit an indication light, the attachment comprising: a sensor body comprising a compliant material that is at least partially translucent in order to allow for at least one of the excitation light, the fluorescent light, and the indication light to pass through, the compliant material formed of material that is electrically and thermally insulating and configured to deform in response to engagement by a surgical tool.

VII. A method for detecting light emitted from brain tissue using an optical sensor system, the optical sensor system comprising an excitation source, a probe comprising at least one fiber coupled to the excitation source, the probe further comprising a compliance member coupled to the at least one fiber and being at least partially translucent, the compliance member including a projection, the probe further comprising an indicator element disposed at least partially within the compliance member, an optical detection module coupled to the at least one fiber and a controller operatively connected to the optical detection module, the method comprising positioning a suction tool such that the projection is near a lumen of the suction tool; applying suction with the suction tool so that the projection becomes disposed within the lumen of the suction tool; and moving the compliance member with the suction tool to a desired position; altering suction of the suction tool such that the suction releases the compliance member; emitting, with the excitation source, excitation light; illuminating, with the at least one fiber, the brain tissue with the excitation light; collecting, with the at least one fiber, fluorescent light from the brain tissue; generating, with the optical detection module, a signal based on the collected fluorescent light; determining, with the controller, a tissue characteristic based on the signal; generating, with the controller, an indicator signal based on the determined tissue characteristic; and emitting light, with the indicator element, in response to receiving the indicator signal.

VIII. A sensor system for detecting a tissue type in a surgical procedure, the sensor system comprising: a probe comprising:

- a compliance member configured to deform in response to engagement by a surgical tool, the compliance member including an electrode;
- an indicator element and configured to emit light in response to receiving an indicator signal;

a detection module coupled to the electrode and configured to generate a detection signal based on electrical signals received by the electrode; and a controller operatively connected to the detection module and configured to determine a tissue characteristic based on the detection signal and generate the indicator signal based on the determined tissue characteristic.

IX. An optical sensor system for detecting a tissue type in a surgical procedure, the optical sensor system comprising: an excitation source configured to selectively emit excitation light; a probe comprising: at least one fiber coupled to the excitation source and configured to illuminate target tissue with excitation light and collect light from target tissue; a compliance member coupled to the at least one fiber, the compliance member being at least partially translucent and configured to deform in response to engagement by a surgical tool, wherein a portion of the at least one fiber is disposed inside of the compliance member; an indicator configured to provide an indication in response to receiving an indicator signal; an optical detection module coupled to the at least one fiber and configured to generate a signal based on the collected light; and a controller operatively connected to the optical detection module and configured to determine a tissue characteristic based on the signal and generate the indicator signal based on the determined tissue characteristic.

X. A method for detecting light emitted from brain tissue using an optical sensor system, the optical sensor system comprising an excitation source, a probe comprising at least one fiber coupled to the excitation source, the probe further comprising a compliance member coupled to the at least one fiber and being deformable, the compliance member being at least partially translucent, the probe further comprising an indicator element disposed at least partially within the compliance member, an optical detection module coupled to the at least one fiber and a controller operatively connected to the optical detection module, the method comprising: engaging the compliance member with a surgical tool such that at least a portion of the compliance member is deformed; moving the compliance member with the surgical tool to a desired position; and emitting, with the excitation source, excitation light; illuminating, with the at least one fiber, the brain tissue with the excitation light; collecting, with the at least one fiber, fluorescent light from the brain tissue; generating, with the optical detection module, a signal based on the collected fluorescent light; determining, with the controller, a tissue characteristic based on the signal;

generating, with the controller, an indicator signal based on the determined tissue characteristic; and emitting light, with the indicator element, in response to receiving the indicator signal.

XI. A sensor system for detecting a tissue type in a surgical procedure, the optical sensor system comprising: a probe comprising:

a member including an electrode or an optical fiber;

an indicator element coupled to the member and configured to emit light in response to receiving an indicator signal;

a detection module coupled to the electrode or the fiber and configured to generate a detection signal based on the signal received by the electrode or the fiber; and a controller operatively connected to the detection module and configured to determine a tissue characteristic based on the signal and generate the indicator signal based on the determined tissue characteristic.

XII. The sensor system of clause XI, wherein the member defines a lumen sized to allow a portion of the surgical tool to be placed therethrough.

XIII. The sensor system of clause XI, wherein the probe includes a connector, and wherein the member is detachable from the at least one probe with the connector, and wherein the member comprises a radiopaque material.

XIV. The sensor system of clause XIII, wherein the radiopaque material comprises gadolinium.

XV. The sensor system of clause XI, wherein the member is bioresorbable.

XVI. The sensor system of clause XI, wherein the member is formed from a material selected from silicone, polyvinylchloride, a hydrogel, a polyurethane, a polysaccharide, cellulose, polylactic acid, and combinations thereof.

XVII. The sensor system of clause XI, wherein the indicator element is disposed with the member.

XVIII. The sensor system of clause XI, wherein the member is further defined as a compliance member.

XIX. The sensor system of clause XVIII, wherein the compliance member has a Rockwell Shore Hardness 00 of 10-50, or a Rockwell Shore Hardness A of 0-20.

What is claimed is:

1. An optical sensor system for detecting a tissue type in a surgical procedure, the optical sensor system comprising:

an excitation source configured to selectively emit excitation light;

a probe comprising:

a co-axial fiber including a central core and an outer channel;

at least one fiber coupled to the excitation source and disposed within the central core of the co-axial fiber, the at least one fiber configured to illuminate target tissue with the excitation light and collect light from target tissue;

a compliance member coupled to the at least one fiber, the compliance member being at least partially translucent and configured to deform in response to engagement by a surgical tool, wherein a portion of the at least one fiber is disposed inside of the compliance member; and an indicator element disposed in the outer channel of the co-axial fiber, the indicator element configured to emit light in response to receiving an indicator signal;

a spectrometer coupled to the at least one fiber and configured to generate a signal based on the collected light from the target tissue; and a controller operatively connected to the spectrometer and configured to determine a tissue characteristic based on the signal and generate the indicator signal based on the determined tissue characteristic.

2. The optical sensor system of claim 1, wherein the compliance member includes a projection extending from an outer surface of the compliance member and sized to be disposed at least partially within a lumen of a suction tool.

3. The optical sensor system of claim 1, wherein the probe further comprises:

a jacket enclosing at least a portion of the co-axial fiber, and a carrier coupled to the jacket and configured to assume different shapes.

4. The optical sensor system of claim 3, wherein:

the carrier is a wire coupled to the jacket between a first portion of the jacket and a second portion of the jacket, and a third portion of the jacket between the first portion and the second portion of the jacket is configured to assume the shape of the carrier.

5. The optical sensor system of claim 3, wherein the probe includes a gripping element coupled to the jacket and being located proximal to the compliance member.

6. The optical sensor system of claim 5, wherein the gripping element includes at least one of:

a fastener configured to attach to a portion of a patient in order prevent movement of the probe from a desired position, and a tab for engagement by the surgical tool for guiding the compliance member into a desired position.

7. The optical sensor system of claim 3, wherein the probe further comprises an anchor coupled to the co-axial fiber or jacket and configured to anchor at least a portion of the co-axial fiber or the jacket to a position, the position being located outside of a patient.

8. The optical sensor system of claim 1, wherein the compliance member comprises a radiopaque material.

9. The optical sensor system of claim 1, wherein the excitation source is further defined as a first excitation source, the optical sensor system further comprising a second excitation source, wherein the indicator element includes an indicator fiber is-coupled to the second excitation source, the second excitation source configured to emit light in response to the indicator signal.

10. The optical sensor system of claim 1, wherein the compliance member defines a lumen sized to allow a portion of the surgical tool to be placed therethrough.

11. The optical sensor system of claim 9, wherein at least one of the first excitation source and the second excitation source is operable in different states, the different states including at least one of an on state, an off state, a first flashing state in which light is emitted at a first frequency, a second flashing state in which light is emitted at a second frequency different than the first flashing state, a first intensity state in which light is emitted at a first intensity, a second intensity state in which light is emitted at a second intensity different than the first intensity, a first color state in which light is emitted at a first color, and a second color state in which light is emitted at second color different than the first color.

12. The optical sensor system of claim 1, wherein:

the compliance member defines a sphere shape; and the compliance member includes a first hemisphere and a second hemisphere, a portion of the co-axial fiber being disposed entirely within at least one of the first hemisphere and the second hemisphere.

13. The optical sensor system of claim 1, wherein a side wall of the outer channel is transparent and configured to allow the indicator element to diffuse light to an ambient area.

14. The optical sensor system of claim 1, wherein:

the probe is configured to illuminate the tissue with the excitation light in a first mode or in a second mode; and in the first mode, the at least one fiber illuminates the tissue with a diffused excitation light and in the second mode, the at least one fiber illuminates the tissue with a focused excitation light.

15. The optical sensor system of claim 14, wherein in the first mode a distal end of the at least one fiber is positioned in a first position relative to a portion of the compliance member and in the second mode the distal end of the at least one fiber is positioned in a second position relative to the portion of the compliance member.

16. An optical sensor system for detecting a tissue type in a surgical procedure, the optical sensor system comprising:

an excitation source configured to selectively emit excitation light;

a probe comprising:

at least one fiber coupled to the excitation source and configured to illuminate target tissue with the excitation light and collect light from target tissue;

a compliance member coupled to the at least one fiber, the compliance member being at least partially translucent and configured to deform in response to engagement by a surgical tool, wherein a portion of the at least one fiber is disposed inside of the compliance member; and an indicator element configured to emit light in response to receiving an indicator signal;

a spectrometer coupled to the at least one fiber and configured to generate a signal based on the collected light from the target tissue; and a controller operatively connected to the spectrometer and configured to determine a tissue characteristic based on the signal and generate the indicator signal based on the determined tissue characteristic, wherein the probe is configured to illuminate the tissue with the excitation light in a first mode or in a second mode, wherein in the first mode, a distal end of the at least one fiber is positioned in a first position relative to a portion of the compliance member and is configured to illuminate the tissue with a diffused excitation light, and wherein in the second mode, the distal end of the fiber is positioned in a second position relative to the portion of the compliance member and is configured to illuminate the tissue with a focused excitation light.

17. The optical sensor system of claim 16, wherein the compliance member comprises a radiopaque material.

18. The optical sensor system of claim 16, wherein the compliance member defines a lumen sized to allow a portion of the surgical tool to be placed therethrough.

19. The optical sensor system of claim 16, wherein the excitation source is further defined as a first excitation source, the optical sensor system further comprising a second excitation source, wherein the indicator element includes an indicator fiber coupled to the second excitation source, the second excitation source configured to emit light in response to the indicator signal.

20. The optical sensor system of claim 19, wherein at least one of the first excitation source and the second excitation source is operable in different states, the different states including at least one of an on state, an off state, a first flashing state in which light is emitted at a first frequency, a second flashing state in which light is emitted at a second frequency different than the first flashing state, a first intensity state in which light is emitted at a first intensity, a second intensity state in which light is emitted at a second intensity different than the first intensity, a first color state in which light is emitted at a first color, and a second color state in which light is emitted at second color different than the first color.

* * * * *